United States Patent
Abramek et al.

(10) Patent No.: US 11,399,833 B2
(45) Date of Patent: Aug. 2, 2022

(54) ANVIL BUTTRESS ATTACHMENT FOR SURGICAL STAPLING APPARATUS

(71) Applicant: Covidien LP, Mansfield, MA (US)

(72) Inventors: Pawel Abramek, Berlin, CT (US); Kenneth M. Cappola, Monroe, CT (US); Matthew J. Chowaniec, Madison, CT (US); Roanit Fernandes, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/073,545

(22) Filed: Oct. 19, 2020

(65) Prior Publication Data

US 2022/0117600 A1    Apr. 21, 2022

(51) Int. Cl.
*A61B 17/072* (2006.01)
*A61B 17/068* (2006.01)

(52) U.S. Cl.
CPC .... *A61B 17/07292* (2013.01); *A61B 17/0686* (2013.01); *A61B 17/072* (2013.01); *A61B 2017/07264* (2013.01); *A61B 2017/07271* (2013.01); *A61B 2017/07285* (2013.01)

(58) Field of Classification Search
CPC .............. A61B 17/0686; A61B 17/072; A61B 17/07207; A61B 17/07292; A61B 17/04; A61B 17/0401; A61B 2017/0053; A61B 2017/07264; A61B 2017/07271; A61B 2017/07285; A61B 2017/07257; A61B 2090/0811; A61B 2017/0406; A61B 2017/2825
USPC ............ 227/175.1–182.1; 606/148, 151, 154
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

European Office Action corresponding to EP 14 17 2681.0 dated May 13, 2016.

(Continued)

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

An anvil buttress loading system includes an anvil assembly, an anvil buttress loading tool, and an anvil buttress. The anvil buttress is retainable on each of the anvil buttress loading tool and the anvil buttress, and is transferrable from the anvil buttress loading tool to the anvil assembly.

20 Claims, 21 Drawing Sheets

(56) References Cited

U.S. PATENT DOCUMENTS

| | | |
|---|---|---|
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |

(56) References Cited

U.S. PATENT DOCUMENTS

| | | |
|---|---|---|
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Farinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |

(56) References Cited

U.S. PATENT DOCUMENTS

| | | |
|---|---|---|
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 10,729,438 B2 * | 8/2020 | Vulhop ............ A61B 17/07292 |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 * | 3/2005 | Dalessandro .... A61B 17/07292 |
| | | 606/151 |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0095791 A1 | 4/2009 | Eskaros et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |

(56) References Cited

U.S. PATENT DOCUMENTS

| | | |
|---|---|---|
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1* | 6/2010 | Olson ............... A61B 17/105 227/176.1 |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256369 A1* | 10/2013 | Schmid ............... A61B 17/068 227/175.1 |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1* | 5/2018 | Aranyi ............. A61B 17/07207 |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1* | 9/2018 | Aranyi ............. A61B 17/072 |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| EP | 3566658 A2 | 11/2019 |
| EP | 3632342 A2 | 4/2020 |
| EP | 3834766 A2 | 6/2021 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |
| WO | WO-2013011965 A1 * | 1/2013 .............. F02P 9/007 |

OTHER PUBLICATIONS

Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 201310706871.0 dated Dec. 16, 2016.
Chinese First Office Action corresponding to CN 201310646606.8 dated Dec. 23, 2016.

(56) References Cited

OTHER PUBLICATIONS

Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.

(56) References Cited

OTHER PUBLICATIONS

Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008 (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated Way 27, 2013; (8 pp).
Extended European Search Report corresponding to EP 12 19 8749.9, completed May 21, 2013 and dated Way 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.

(56) References Cited

OTHER PUBLICATIONS

Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
International Search Report dated May 13, 2022 and Written Opinion completed Jan. 20, 2022 corresponding to counterpart Int'l Patent Application PCT/US2021/055376.

* cited by examiner

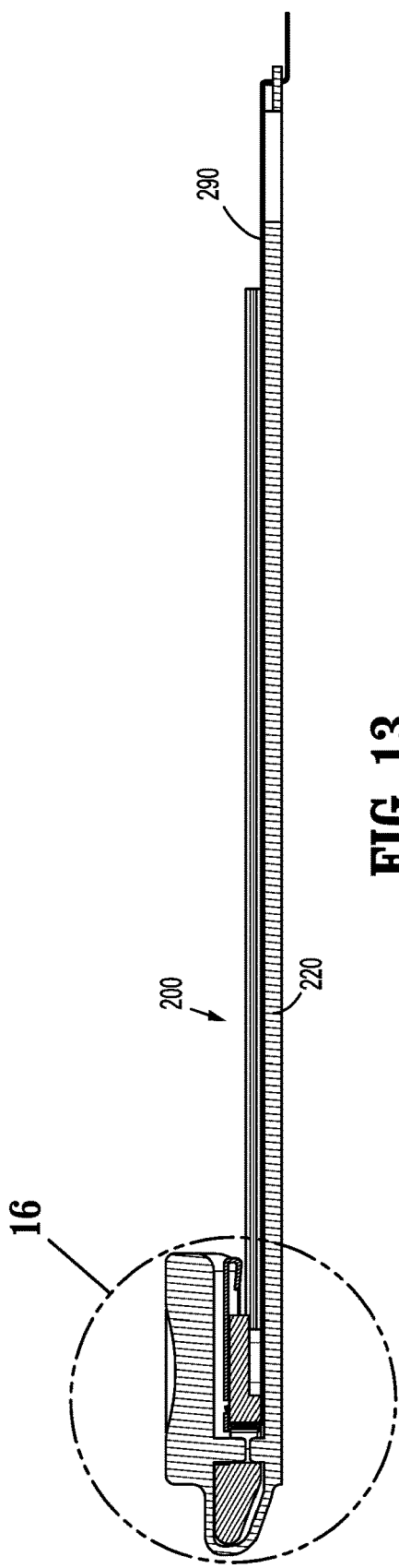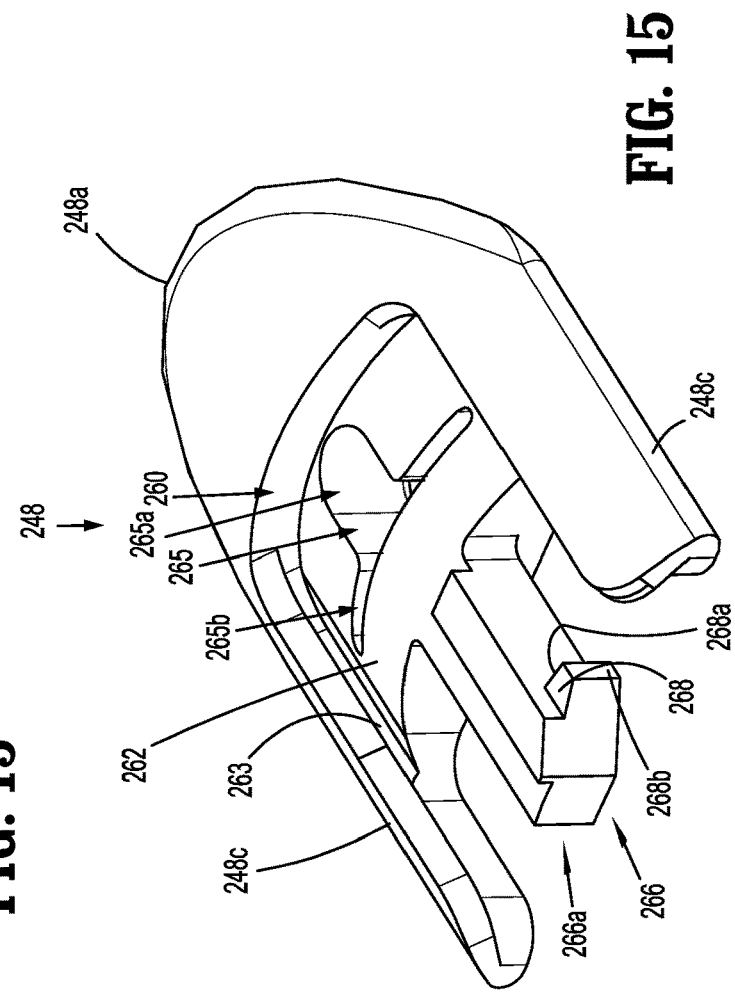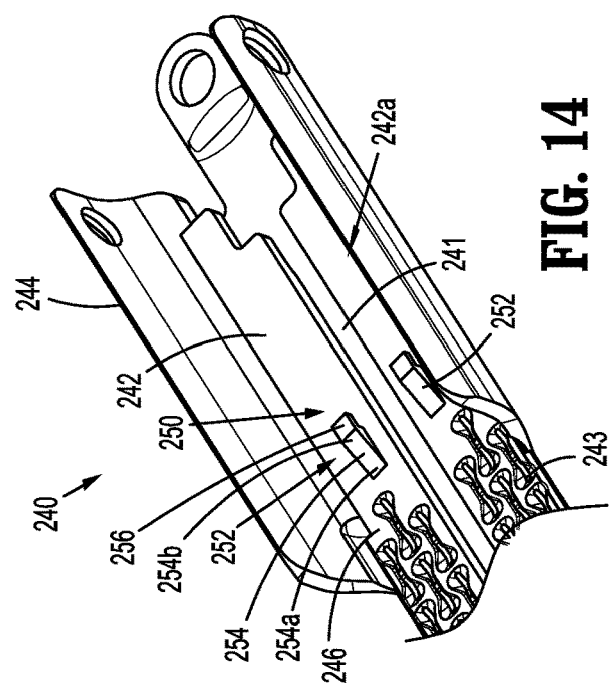
FIG. 13
FIG. 14
FIG. 15

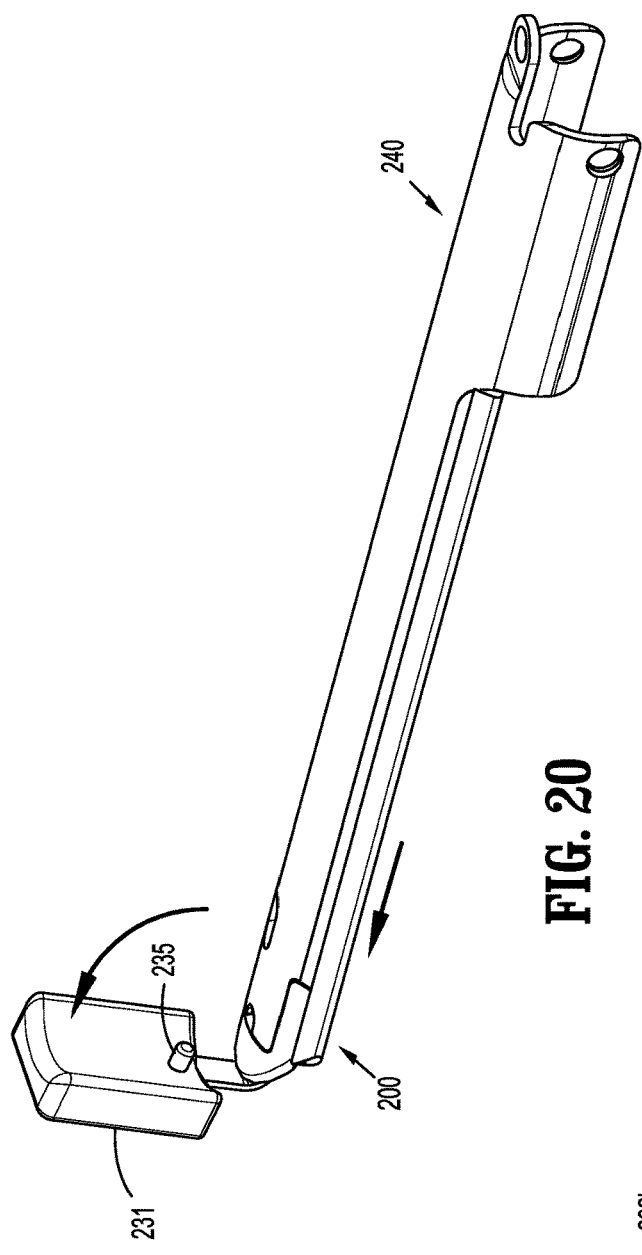
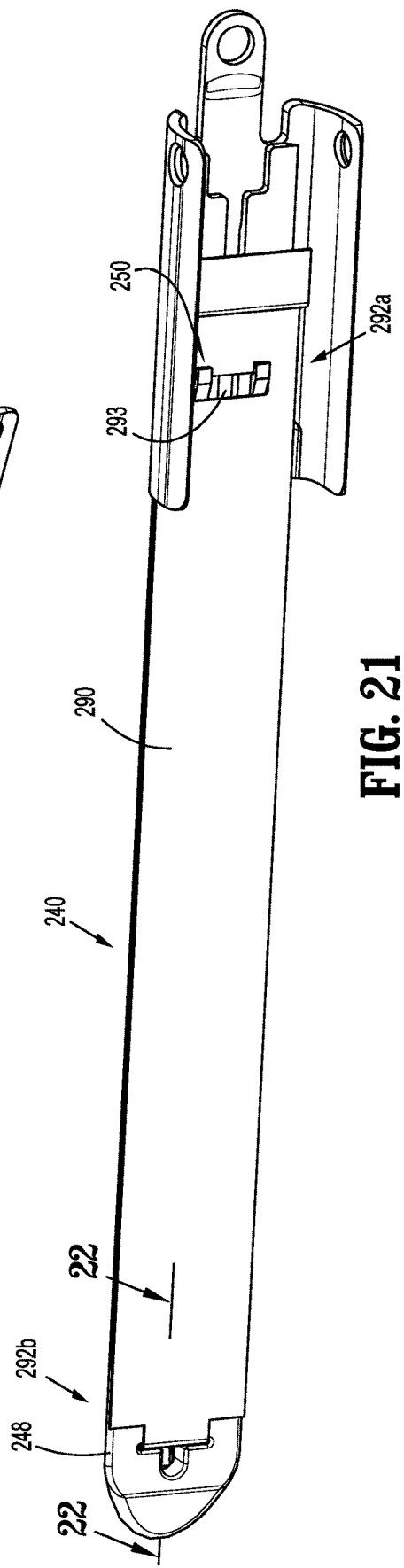

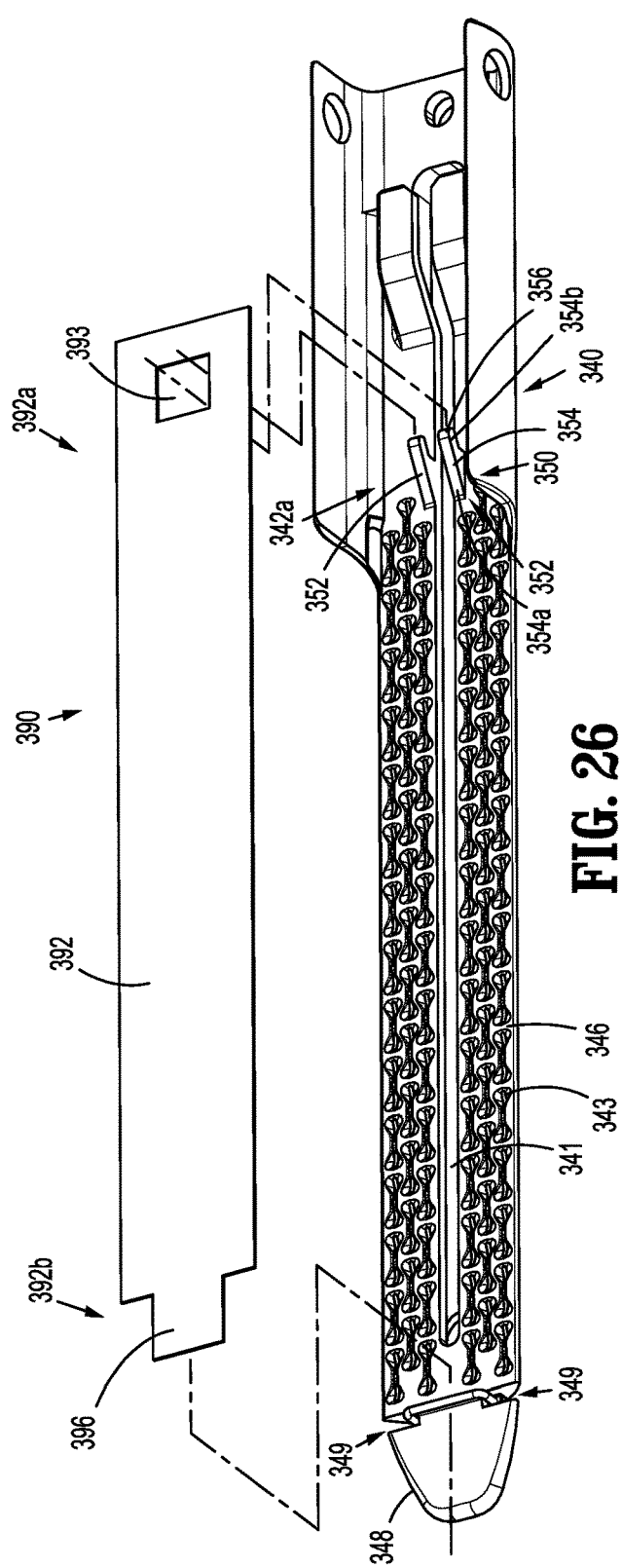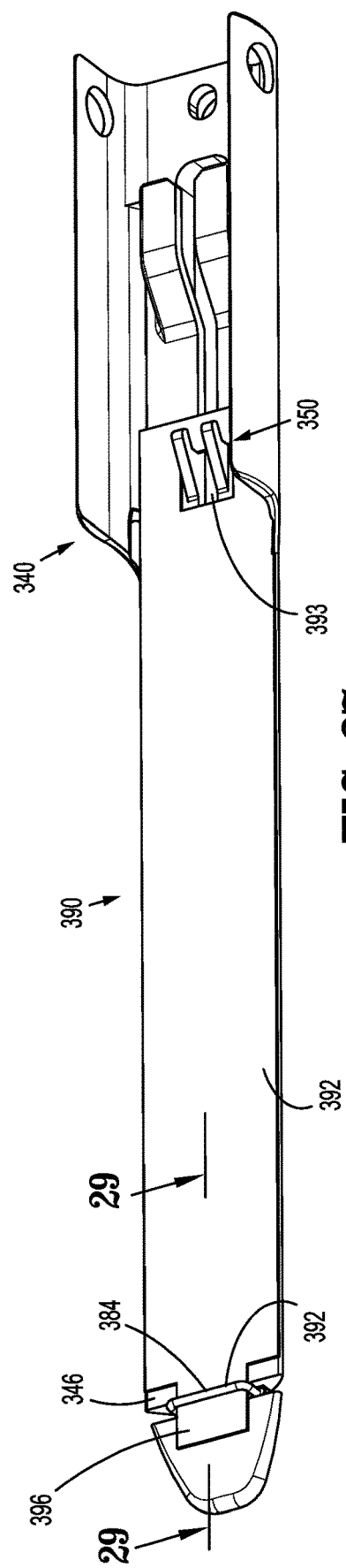
FIG. 26
FIG. 27

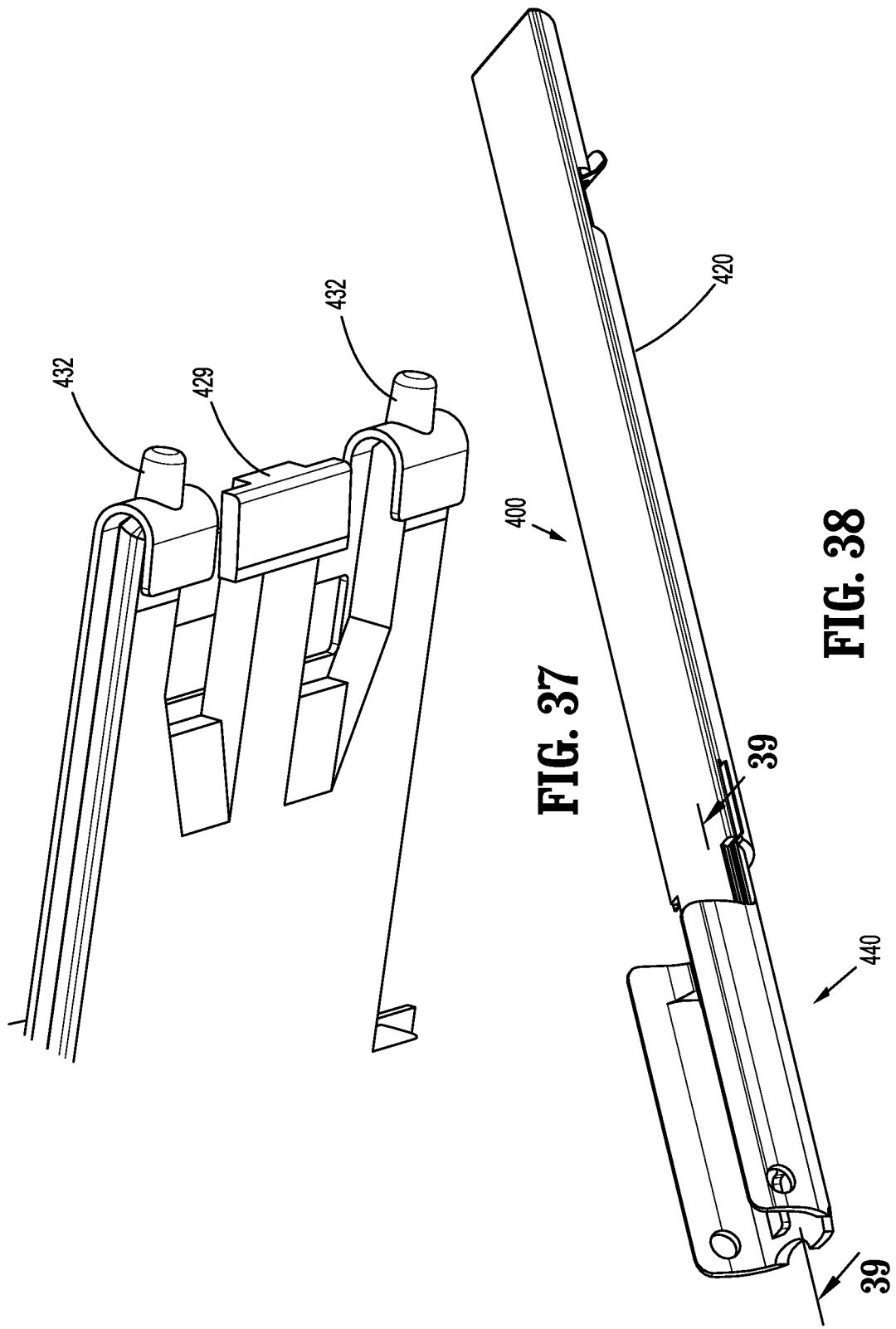

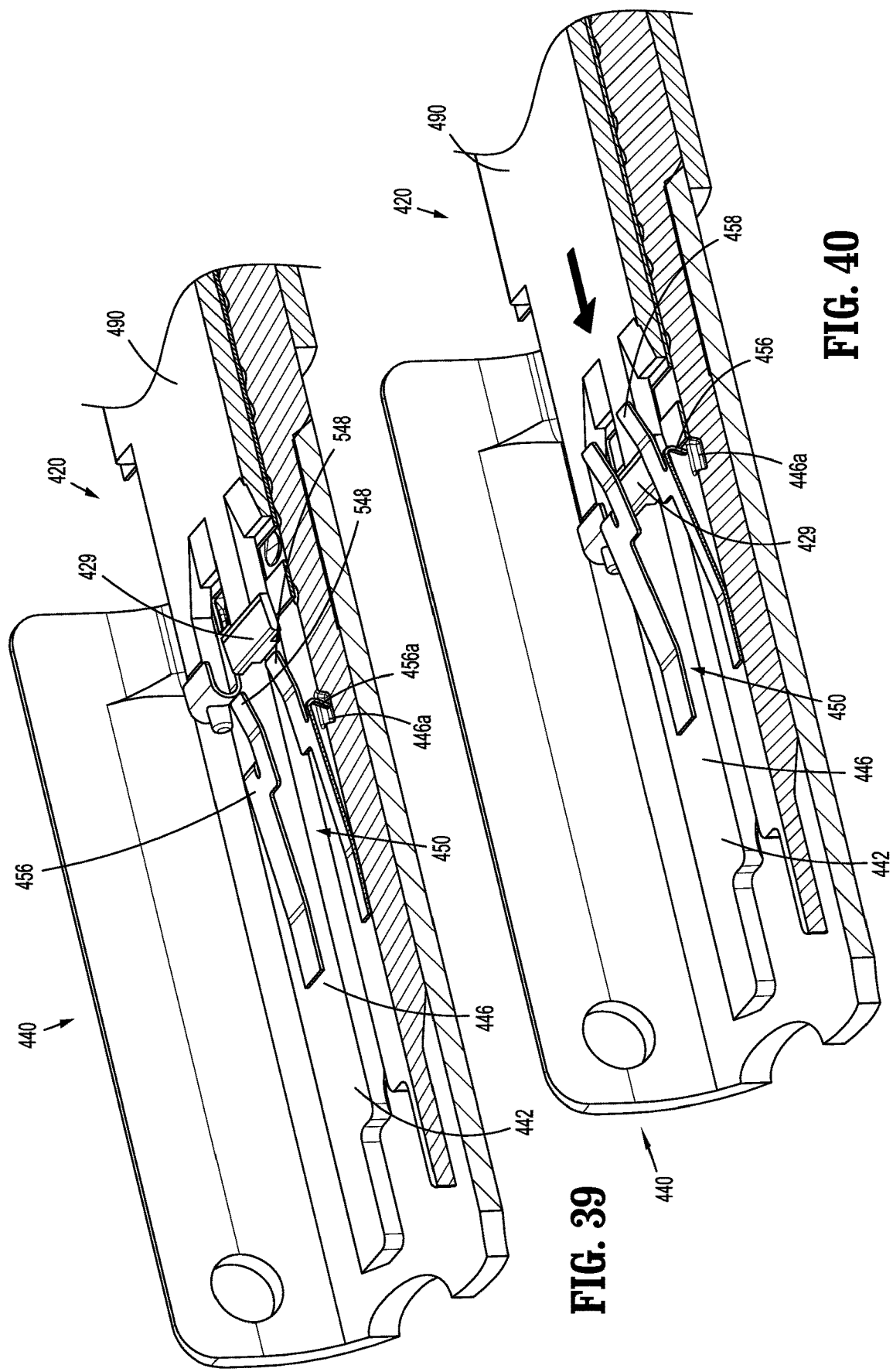

ANVIL BUTTRESS ATTACHMENT FOR SURGICAL STAPLING APPARATUS

FIELD

The present application is generally related to surgical stapling apparatus, and more particularly, to anvil buttresses, anvil assemblies including anvil buttress attachment assemblies, and anvil buttress loading tools for releasably securing the anvil buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon, e.g., by an expensive automated attachment process. The buttress material reinforces the staple or suture line as well as covers the juncture of the tissues to reduce leakage prior to healing.

SUMMARY

The present disclosure relates to anvil side buttress material attachment onto a loading unit of a surgical stapling apparatus. Anvil buttresses, anvil assemblies including anvil buttress attachment assemblies, and anvil buttress loading tools are designed to make anvil buttress attachment in the operating room a simple, straightforward, and cost effective procedure. For example, the anvil buttresses, anvil assemblies, and anvil buttress loading tools are configured for mechanical engagement of the anvil buttress to either of the anvil assembly or the anvil buttress loading tool, and for the transfer of the anvil buttress from the anvil buttress loading tool to the anvil assembly by sliding the anvil buttress loading tool, loaded with the anvil buttress, on to and off of the anvil assembly. Such configurations, as compared, for example, to attachment systems requiring the use of adhesives, reduce the number of components and/or assembly steps required to use the surgical stapling apparatus with an anvil buttress thereby simplifying the set-up and/or use of the surgical stapling apparatus and reducing time and/or cost to the user. As another example, the anvil buttress loading tools may be pre-loaded (e.g., by the manufacturer or prior to use in the operating room) with an anvil buttress so that a user need only load the anvil assembly with the anvil buttress via the loading tool which also simplifies the set-up and/or use of the surgical stapling apparatus and reduces the time and/or cost of the surgical procedure.

In one aspect, the present disclosure provides an anvil buttress loading system including an anvil assembly, an anvil buttress loading tool, and an anvil buttress. The anvil assembly includes an anvil plate and an anvil tip. The anvil plate has a tissue facing surface defining a plurality of staple forming pockets therein, and a proximal end portion of the tissue facing surface includes a hook assembly. The anvil buttress loading tool includes a carrier defining a cavity therein. The carrier has a support surface, with a proximal end portion of the carrier including a pair of proximal protrusions and a distal end portion of the carrier including a distal protrusion. The anvil buttress includes a body, a pair of proximal tabs extending proximally from the body, and a distal tab extending distally from the body. The body of the anvil buttress is positionable on the support surface of the anvil buttress loading tool with the pair of proximal tabs engaged with the pair of proximal protrusions and the distal tab engaged with the distal protrusion to retain the anvil buttress on the anvil buttress loading unit. The body of the anvil buttress is positionable on the tissue facing surface of the anvil assembly with a proximal end portion of the body engaged with the hook assembly and a distal end portion engaged with the anvil tip to retain the anvil buttress on the anvil assembly. The anvil buttress is transferrable from the anvil buttress loading tool to the anvil assembly.

The hook assembly of the anvil assembly may include a pair of hooks disposed on opposed sides of a central longitudinal slot defined through the tissue facing surface. Each hook may include an arm having a first end anchored to the tissue facing surface and a second end including a finger extending therefrom. The first end of the arm may be anchored to the tissue facing surface at a proximal end thereof and the second end of the arm may be disposed distal thereto. A terminal end of the finger may be biased against the tissue facing surface of the anvil assembly and movable relative to the tissue facing surface.

The anvil buttress may have a proximal window defined in the proximal end portion of the body. The proximal window may be configured to receive the fingers of the pair of hooks therethrough. The anvil buttress may have a distal window defined through a distal end portion of the anvil buttress. The distal window may be configured to receive the anvil tip therethrough.

The carrier of the anvil buttress loading tool may include longitudinal rails extending from opposed sides of the support surface. The anvil assembly may be positionable between the longitudinal rails with the tissue facing surface adjacent to the support surface. The carrier of the anvil buttress loading tool may include a transverse rail extending across distal ends of the longitudinal rails and over the support surface defining a distal opening into the cavity.

In another aspect, the disclosure provides an anvil buttress loading assembly including an anvil buttress loading tool and an anvil buttress. The anvil buttress loading tool includes a carrier defining a cavity therein. The carrier has a support surface, with a proximal end portion of the carrier including a pair of proximal protrusions and a distal end portion of the carrier including a distal protrusion. The anvil buttress includes a body, a pair of proximal tabs extending proximally from the body, and a distal tab extending distally from the body. The body of the anvil buttress is positioned on the support surface, the pair of proximal tabs are engaged with the pair of proximal protrusions, and the distal tab are engaged with the distal protrusion.

The carrier of the anvil buttress loading tool may include longitudinal rails extending from opposed sides of the support surface. A plurality of axially spaced and opposed tabs may extend from the longitudinal rails and over the support surface. The carrier of the anvil buttress loading tool may include a transverse rail extending across distal ends of the longitudinal rails and over the support surface defining a distal opening into the cavity. The distal protrusion may extend from the transverse rail. The anvil buttress may include a distal window defined through a distal end portion of the body, with the distal window aligned with the distal opening of the carrier.

In yet another aspect, the disclosure provides a loading unit including a staple cartridge assembly, an anvil assembly, and an anvil buttress. The anvil assembly includes an anvil plate and an anvil tip. The anvil plate has a tissue facing surface defining a plurality of staple forming pockets therein, with a proximal end portion of the tissue facing surface including a hook assembly. The anvil buttress includes a body having a proximal end portion releasably coupled to the anvil assembly by the hook assembly.

The hook assembly may include a pair of hooks disposed on opposed sides of a central longitudinal slot defined through the tissue facing surface of the anvil assembly. Each hook may have an arm having a first end anchored to the tissue facing surface and a second end including a finger extending therefrom. The first end of the arm may be anchored to the tissue facing surface at a proximal end thereof and the second end of the arm may be disposed distal thereto. A terminal end of the finger may be biased against the tissue facing surface of the anvil assembly and movable relative to the tissue facing surface.

The anvil buttress may have a proximal window defined in the proximal end portion of the body, with the fingers of the pair of hooks extending through the proximal window and positioned against the tissue facing surface. The anvil buttress may have a distal window defined through a distal end portion of the body, with the distal end portion of the anvil buttress coupled to the anvil assembly by engagement of the distal window around the anvil tip.

The details of one or more aspects of the disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

FIG. 13 is a cross-sectional view of the anvil buttress loading tool of FIG. 11, taken along section line 13-13 of FIG. 11;

FIG. 14 is a bottom, perspective view of a proximal end portion of the anvil assembly of FIG. 11;

FIG. 15 is a top perspective view of the anvil tip of FIG. 11;

FIG. 20 is a perspective view of the anvil assembly and the anvil buttress loading tool of FIG. 18, shown with a retainer of the anvil buttress loading tool being removed from the anvil plate;

FIG. 21 is a bottom, perspective view of the anvil assembly of FIG. 20 loaded with the anvil buttress;

FIG. 26 is a bottom, perspective view, with parts separated, of the anvil assembly of FIG. 25 and an anvil buttress;

FIG. 27 is a bottom, perspective view of the anvil buttress of FIG. 26 loaded onto the anvil assembly;

FIG. 37 is a close-up view of a proximal end portion of the anvil buttress loading tool and the anvil buttress of FIG. 36;

FIG. 38 is a bottom, perspective view of the anvil assembly of FIG. 33 loaded with the anvil buttress;

FIGS. 39-41 are partial cross-sectional views of the anvil assembly and the anvil loading tool of FIG. 33, shown during loading of the anvil buttress onto the anvil assembly.

DETAILED DESCRIPTION

Figure 1:
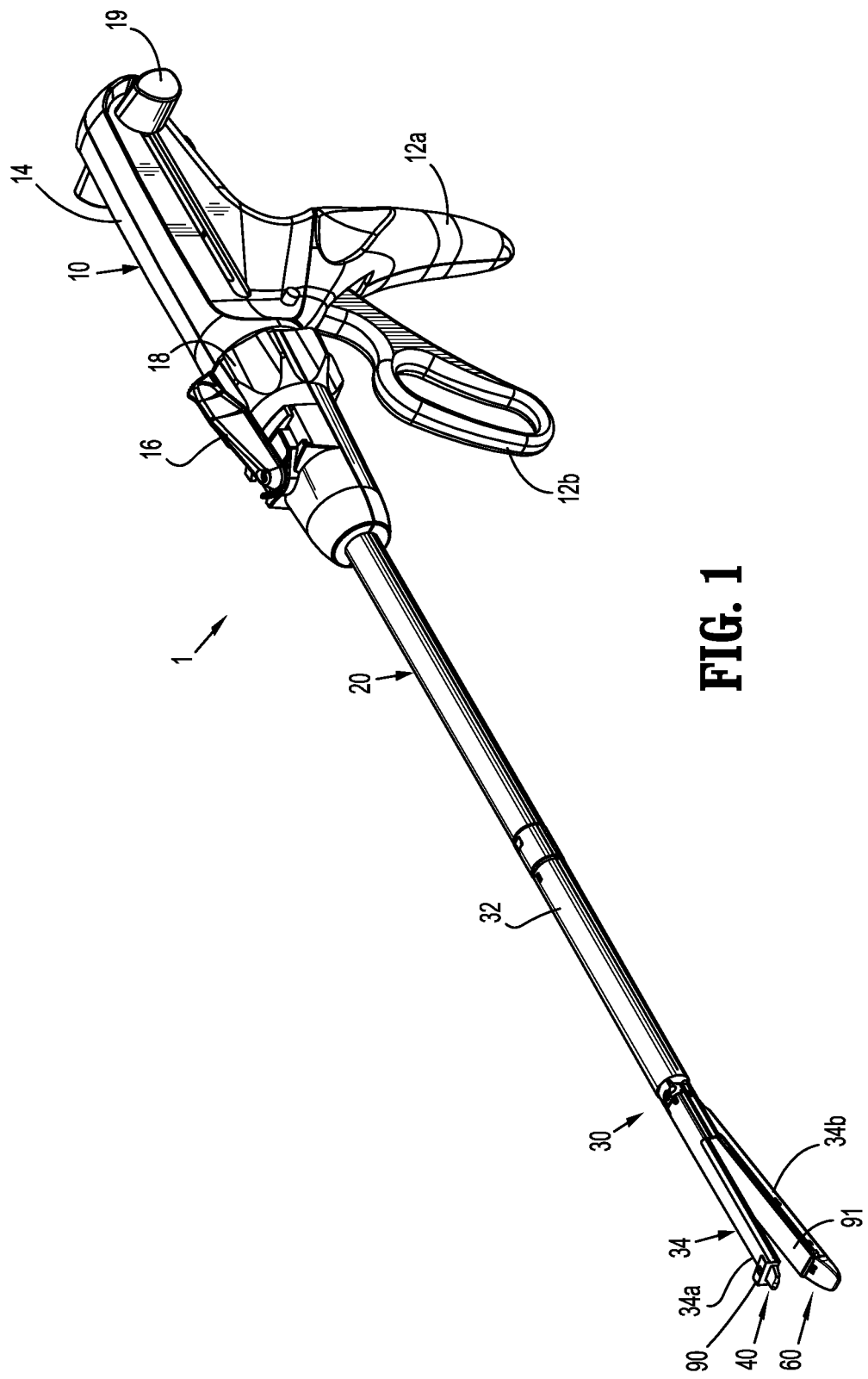
FIG. 1 is a perspective view of a surgical stapling apparatus in accordance with an aspect of the present disclosure.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user.

Referring now to FIG. 1, an exemplary surgical stapling apparatus or surgical stapler 1 is shown for use in stapling tissue in accordance with aspects of the present disclosure. The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples 70 (FIG. 2) to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A pair of knobs 19 is movably positionable along the barrel portion 14. The pair of knobs 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

Figure 2:
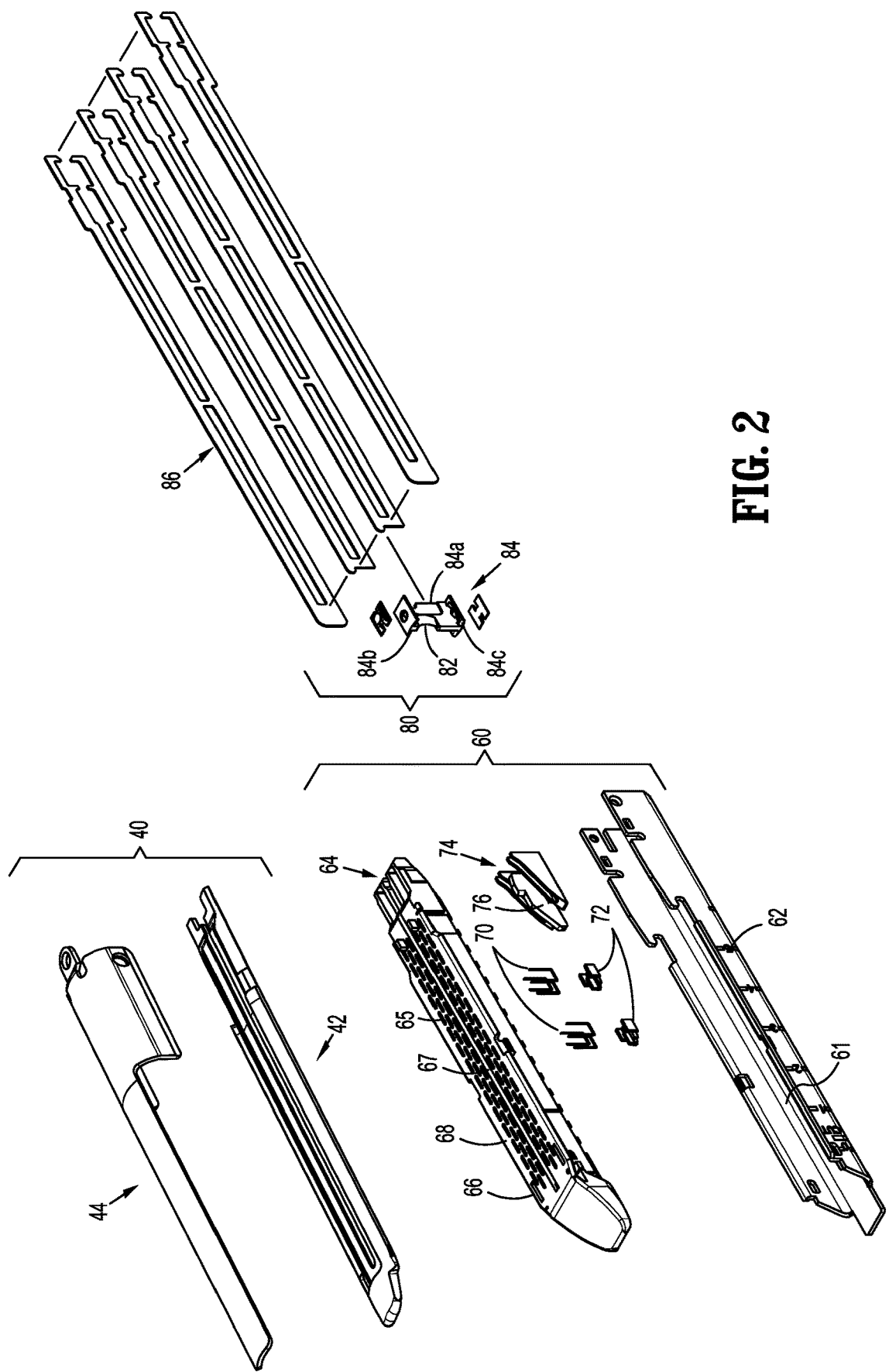
FIG. 2 is an exploded, perspective view of a tool assembly of the surgical stapling apparatus of FIG. 1.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 64 as seen in FIG. 2) of the MULU is replaced after each staple and cut operation of the surgical stapling apparatus 1 a pre-determined number of times before the entire MULU needs to be replaced. Alternatively, the loading unit 30 may be permanently affixed to the elongated tubular body 20.

Figure 3:
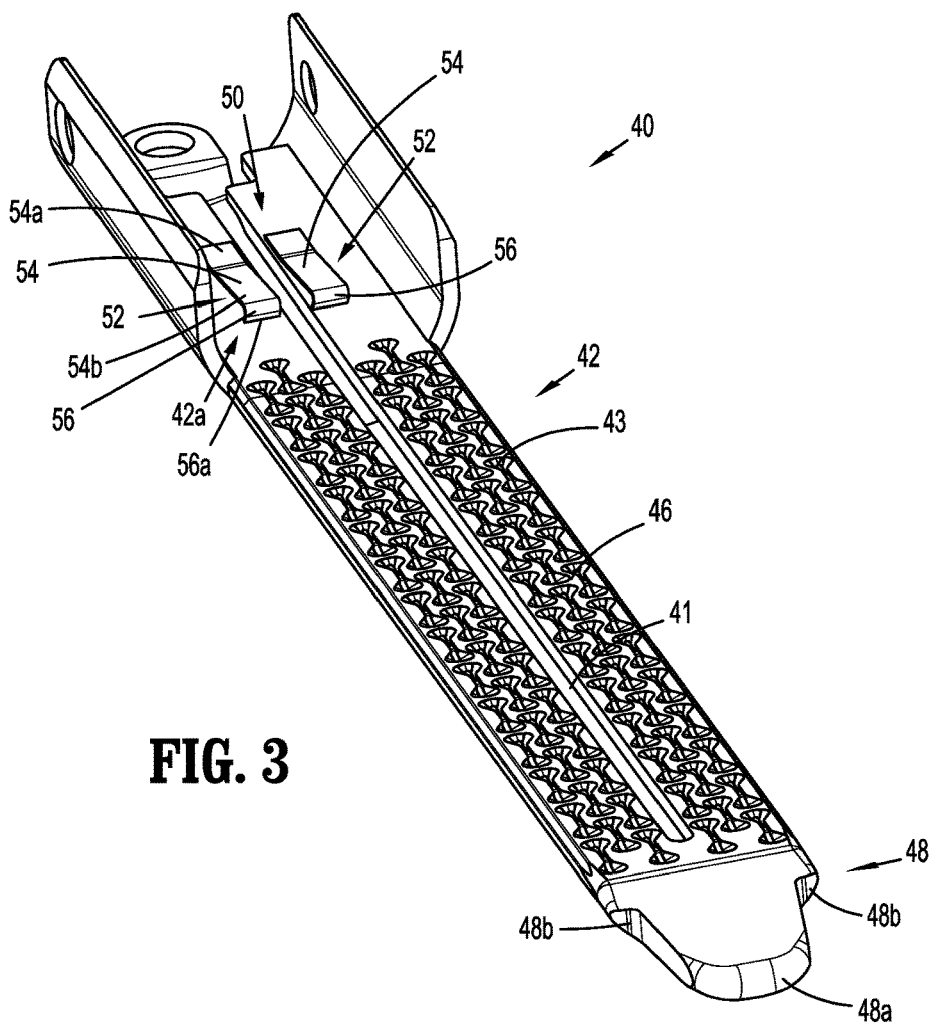
FIG. 3 is a bottom, perspective view of an anvil assembly of the tool assembly of FIG. 2.

As shown in FIGS. 1 and 2, the first jaw member 34a of the tool assembly 34 includes an anvil assembly 40 and the second jaw member 34b of the tool assembly 34 includes a staple cartridge assembly 60. The anvil assembly 40 includes an anvil plate 42 and a cover plate 44 secured over the anvil plate 42. As seen in FIG. 3, in conjunction with FIG. 2, the anvil plate 42 has a central longitudinal slot 41 formed therein and a plurality of staple forming pockets or cavities 43 defined in an inward or tissue facing surface thereof 46, with an anvil tip 48 extending distal to the staple forming pockets 43. The tissue facing surface 46 is substantially planar along the length having the staple forming pockets 43 defined therein and angled outwardly or tapering towards an outer surface 45 of the anvil assembly 40 through the anvil tip 48. The anvil tip 48 has a curved leading end 48a and a pair of shoulders 48b disposed on opposed sides of the anvil tip 48. The pair of shoulders 48b are distally facing and configured to provide a stop surface for securing a distal end portion of a surgical buttress thereto. A proximal portion 42a of the anvil plate 42, which extends proximally of the staple forming pockets 43, includes a hook assembly 50 configured to secure a proximal end portion of a surgical buttress thereto.

With continued reference to FIG. 3, the hook assembly 50 includes a pair of hooks 52, with each hook 52 disposed on opposed sides of the central longitudinal slot 41. Each hook 52 includes an arm 54 having a first or proximal end portion 54a anchored or secured to the tissue facing surface 46 of the anvil plate 42 and a second or distal end portion 54b including a finger 56 extending therefrom. The finger 56 is bent or curved relative to the arm 54 such that a terminal end 56a of the finger 56 is biased against (e.g., in direct contact with) the tissue facing surface 46 of the anvil plate 42. Each hook 52 is hingedly or springedly connected to the anvil plate 52 at the proximal end portion 54a thereof such that the finger 56 is movable away from (e.g., capable of being raised off of) the tissue facing surface 46 upon application of a force thereto. In aspects, the pair of hooks 52 are leaf spring hooks, however, other cantilever hook configurations including, for example, a flexible arm and a rigid finger are contemplated.

With reference again to FIG. 2, the staple cartridge assembly 60 includes a cartridge carrier 62 defining an elongated support channel 61 configured and dimensioned to selectively receive and support a staple cartridge 64 therein.

The staple cartridge 64 may be removably and/or replaceably attached to the cartridge carrier 62 by, for example, a snap-fit connection, a detent, a latch, among other types of connectors within the purview of those skilled in the art. The staple cartridge 64 includes a cartridge body 66 having an inward or tissue facing surface 68 defining staple pockets or retention slots 65 formed therein for receiving a plurality of fasteners or staples 70 and staple pushers 72. A central longitudinal slot 67 is formed in and extends along a substantial length of the cartridge body 66 to facilitate passage of a knife blade 82 of a drive assembly 80 therethrough.

The knife blade 82 is defined in a distal edge of a central wall portion 84a of an I-beam 84 that is operatively associated with the tool assembly 34. The central wall portion 84a of the I-beam 84 is slidably disposed between the anvil and staple cartridge assemblies 40, 60, with upper and lower rails 84b, 84c of the I-beam 84, respectively, supported in the anvil and staple cartridge assemblies 40, 60. The I-beam 84 is coupled to an elongated drive beam 86 which is configured to engage a drive member (not shown) of the elongated tubular body 20 (FIG. 1) of the surgical stapling apparatus 1 when the loading unit 30 is engaged therewith. The drive member imparts axial movement to the elongated drive beam 86 and thus, the I-beam 84, from the handle assembly 10. Accordingly, during operation of the surgical stapling apparatus 1, distal advancement of the I-beam 84 causes an actuation sled 74 to translate through the staple cartridge 64 and to advance cam wedges 76 of the actuation sled 74 into sequential contact with the staple pushers 72 which, in turn, cause the staple pushers 72 to translate vertically within the staple pockets 65 and urge the staples 70 from the staple pockets 65 towards the tissue facing surface 46 of the anvil plate 42 of the anvil assembly 40.

For a detailed description of the structure and function of exemplary surgical stapling apparatus, reference may be made to U.S. Pat. Nos. 6,241,139, 6,330,965, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with aspects of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with aspects of the present disclosure.

Figure 4:
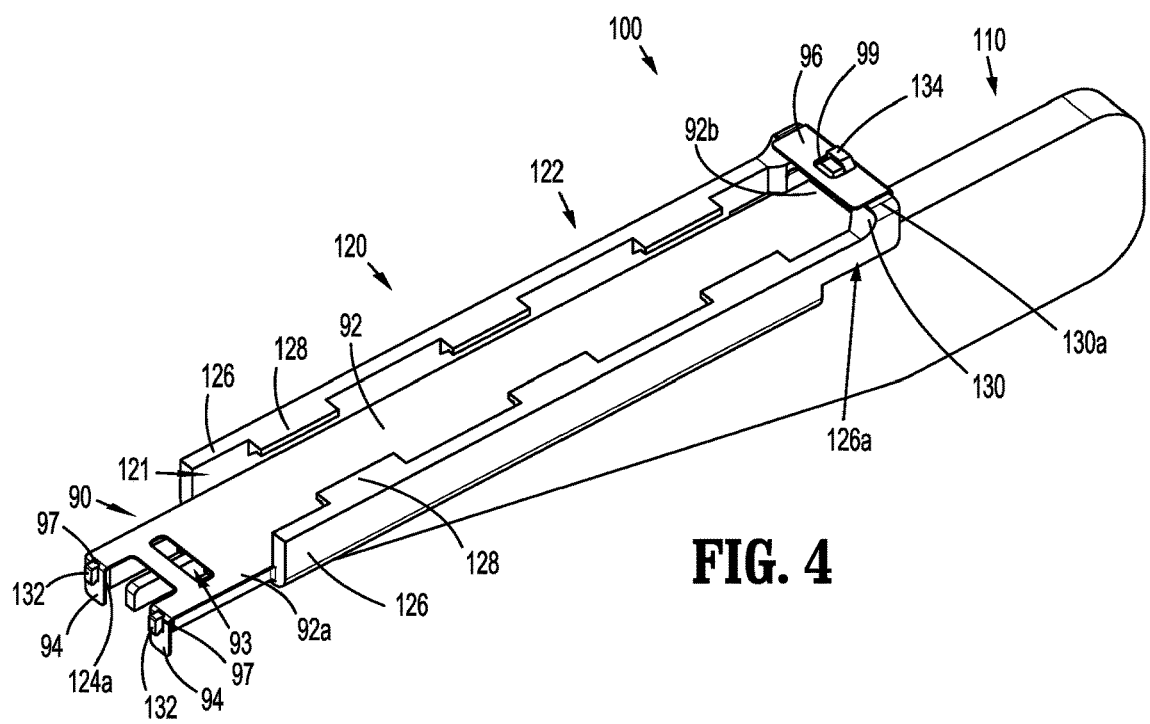
FIG. 4 is a perspective view of an anvil buttress loading tool, loaded with an anvil buttress, in accordance with an aspect of the present disclosure.

Turning now to FIG. 4, an anvil buttress 90 (also referred to herein generally as a surgical buttress) is shown loaded within an anvil buttress loading tool 100 (also referred to herein as a loading tool). The anvil buttress 90 includes a body 92 having a first or proximal window 93 defined through a proximal end portion 92a of the body 92 and a second or distal window 95 (FIG. 5) defined through a distal end portion 92b of the body 92. A pair of proximal tabs 94 extend proximally from the proximal end portion 92a of the body 92, with each tab 94 defining an opening 97 therethrough. A distal tab 96 extends distally from the distal end portion 92b of the body 92 and defines an opening 99 therethrough.

The anvil buttress 90 is fabricated from biocompatible materials which are bioabsorbable or non-absorbable, natural or synthetic materials. It should be understood that a single or combination of natural, synthetic, bioabsorbable, and/or non-bioabsorbable materials may be used to form the anvil buttress 90. In aspects, the anvil buttress 90 is formed from a single sheet of material that is cut to shape. In other aspects, the anvil buttress 90 is formed from a plurality of sheets of material, that are fabricated from the same or different materials, and/or the components (e.g., the body, the tabs, etc.) of the anvil buttress 90 are formed from the same or different materials that are attached to one another by, for example, welding, using adhesive, tying sutures, etc.

The anvil buttress 90 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The anvil buttress 90 may be a single porous or non-porous layer, or include a plurality of layers including any combination of porous and non-porous layers. For example, the anvil buttress may include multiple porous and non-porous layers that are stacked in an alternating manner. In another example, the anvil buttress may be formed in a "sandwich-like" manner wherein the outer layers are porous and the inner layer(s) are non-porous, or vice versa.

Porous layer(s) in a surgical buttress may enhance the ability of the surgical buttress to absorb fluid, reduce bleeding, and/or seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

With continued reference to FIG. 4, the anvil buttress loading tool 100 includes a handle 110 and a carrier 120 secured to the handle 110. The handle 110 is configured for grasping by a user and the carrier 120 is configured to releasably retain the anvil buttress 90 therein and to receive the anvil assembly 40 (FIG. 3) for loading of the anvil buttress 90 thereon. The carrier 120 includes a housing 122 having a support surface 124 (FIG. 7), longitudinal rails 126 extending from opposed sides of the support surface 124, and a plurality of axially spaced and opposed tabs 128 extending from the longitudinal rails 126 and over the support surface 124. A cavity 121 is defined in the carrier 120 by the support surface 124, the longitudinal rails 126, and the tabs 128. A transverse rail 130 extends across distal ends 126a of the longitudinal rails 126 and over the support surface 124. The transverse rail 130 is disposed in spaced relation relative to the support surface 124 and defines a distal opening 125 (FIG. 5) into the cavity 121. A pair of proximal protrusions 132 extend proximally from a proximal end 124a of the support surface 124, and a distal protrusion 134 extends outwardly from an outer surface 130a of the transverse rail 130.

Figure 5:
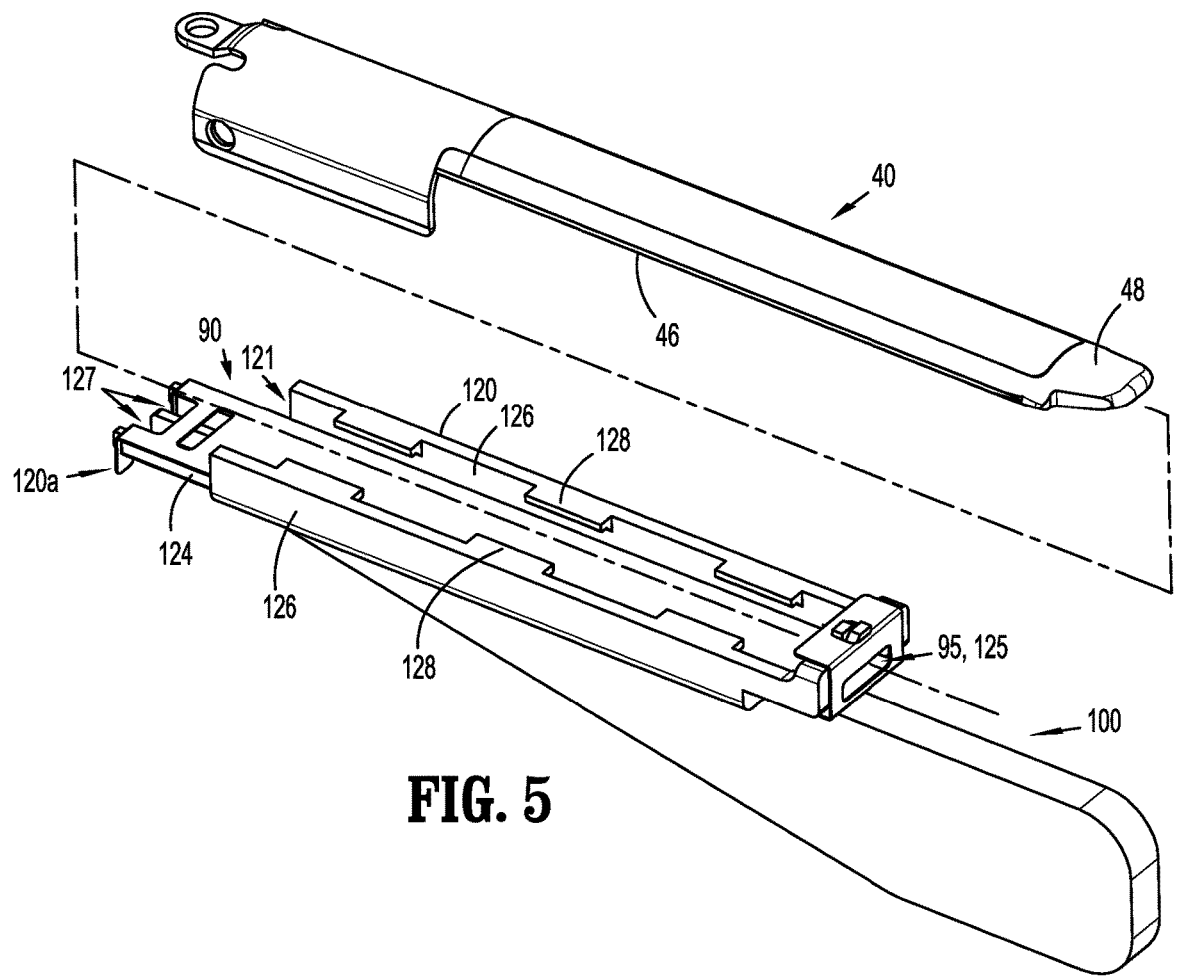
FIG. 5 is a perspective view, with parts separated, of the anvil assembly of FIG. 3 and the anvil buttress loading tool of FIG. 4.

In a method of loading the loading tool 100 with the anvil buttress 90, the body 92 of the anvil buttress 90 is placed against the support surface 124 of the carrier 120. With the body 92 of the anvil buttress 90 positioned on the support surface, 124, the pair of proximal tabs 94 at the proximal end portion 92a of the body 92 is aligned or in registration with the pair of proximal protrusions 132 on the proximal end 124a of the support surface 124, and the distal tab 96 at the distal end portion 92b of the body 92 is aligned or in registration with the distal protrusion 134 of the transverse rail 130. The proximal and distal end portions 92a, 92b of the anvil buttress 90 are manipulated to engage the pair of proximal tabs 94 with the pair of proximal protrusions 132 and the distal tab 96 with the distal protrusion 134. As seen in FIG. 5, in the loaded configuration, the distal window 95 defined through the anvil buttress 90 is aligned with the distal opening 125 of the loading tool 100. It should be understood that other attachment features are contemplated for securing the tabs of the anvil buttress to the carrier of the loading tool.

Figure 6:
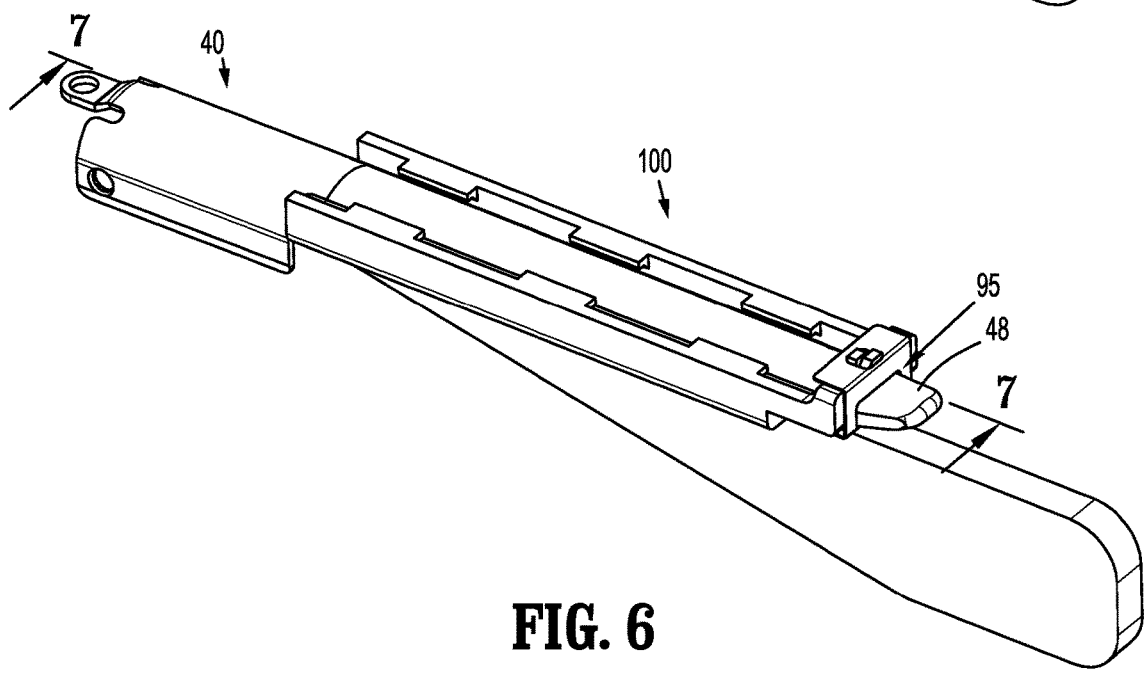
FIG. 6 is a perspective view of the anvil assembly of FIG. 5 advanced into the anvil buttress loading tool of FIG. 5.
Figure 7:
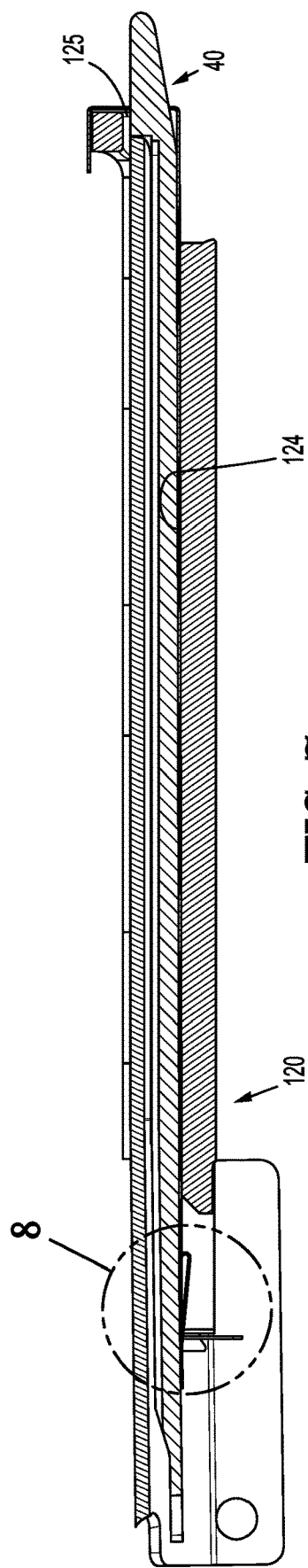
FIG. 7 is a cross-sectional view of the anvil assembly and the anvil buttress loading tool of FIG. 6, taken along section line 7-7 of FIG. 6.
Figure 8:
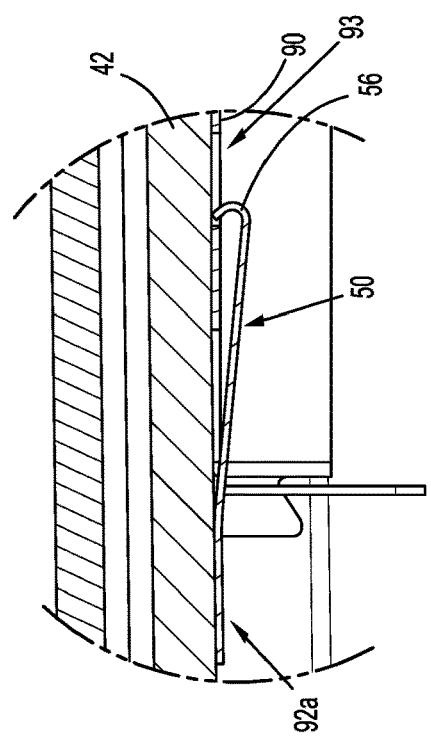
FIG. 8 is a close-up view of a proximal portion of the anvil assembly and the anvil buttress loading tool of FIG. 7, shown with a hook assembly of the anvil assembly engaged with the anvil buttress.

As shown in FIGS. 5-8, in a method of loading the anvil assembly 40 with the anvil buttress 90, the anvil tip 48 of the anvil assembly 40 is aligned with a proximal end 120a of the carrier 120 of the loading tool 100. The anvil assembly 40 is slid distally into the cavity 121 of the carrier 120 such that the tissue facing surface 46 of the anvil assembly 40 is adjacent to or in contact with the anvil buttress 90. The anvil assembly 40 is guided through and retained within the cavity 121 of the carrier 120 by the support surface 124, the longitudinal rails 126, and the plurality of tabs 128. The anvil assembly 40 is slid distally until the anvil tip 48 extends through the distal window 95 defined through the anvil buttress 90, as seen in FIG. 6, the pair of shoulders 48b (FIG. 3) of the anvil tip 48 acting as stop surfaces to the distal movement. During this sliding movement, the hook assembly 50 slides into openings 127 (FIG. 5) defined in the proximal end 124a of the support surface 124 and captures the proximal end portion 92a of the anvil buttress 90, as seen in FIGS. 7 and 8, through placement of the fingers 56 within the proximal window 93 of the anvil buttress 90. It should be understood that additionally or alternatively, the loading tool 100 may be slid proximally relative to the anvil assembly 40.

Once the anvil assembly 40 is fully advanced into the carrier 120 of the loading tool 100, as seen in FIG. 6, the loading tool 100 may be separated from the anvil assembly 40 by sliding the loading tool 100 and/or the anvil assembly 40 away from each other. As the anvil assembly 40 and the loading tool 100 are separated from each other, the proximal and distal end portions 92a, 92b of the body 92 of the anvil buttress 90 disengage from the proximal and distal protrusions 132, 134 of the carrier 120.

Figure 9:
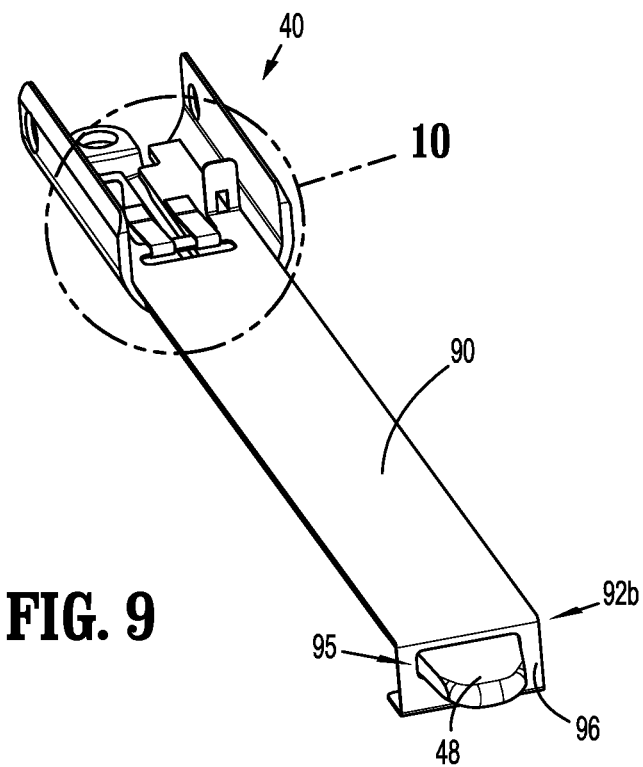
FIG. 9 is a bottom, perspective view of the anvil assembly of FIG. 6 loaded with the anvil buttress.
Figure 10:
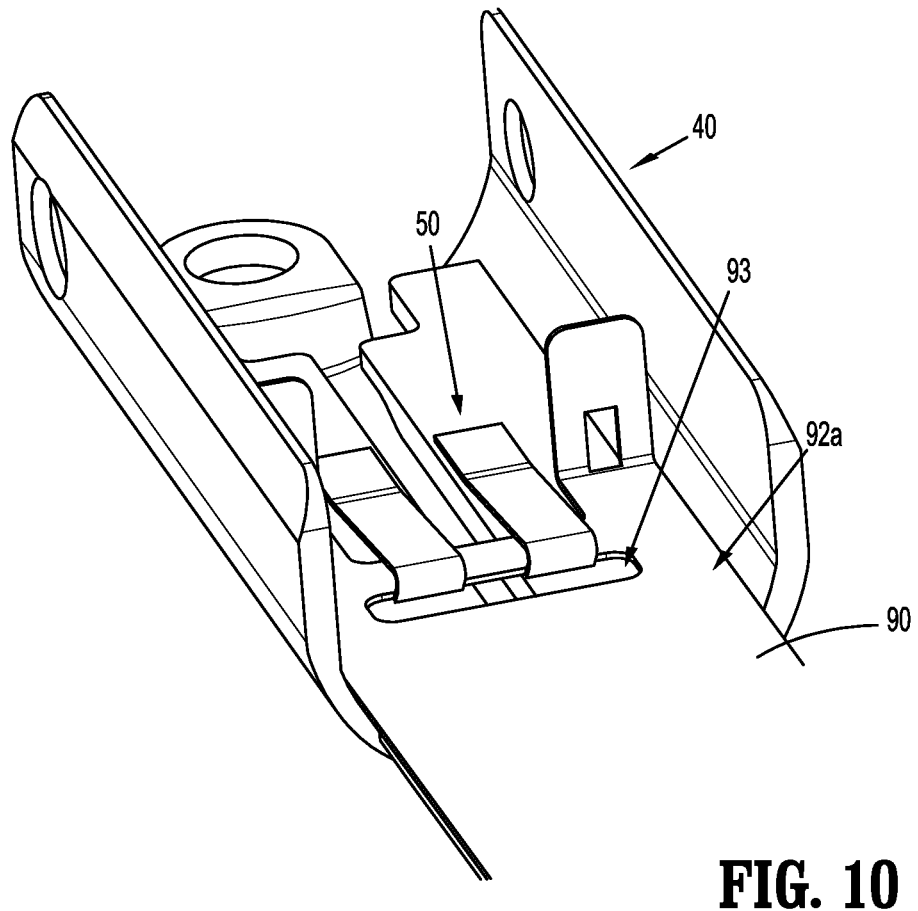
FIG. 10 is a close-up view of a proximal portion of the anvil assembly and the anvil buttress of FIG. 9, shown with a hook assembly of the anvil assembly engaged with a proximal window defined through the anvil buttress.

As shown in FIGS. 9 and 10, the proximal end portion 92a of the anvil buttress 90 is retained on the anvil assembly 40 by engagement of the hook assembly 50 through the proximal window 93 and the distal end portion 92b of the anvil buttress 90 is retained on the anvil assembly 40 by engagement of the anvil tip 48 with the distal tab 96 through the distal window 95. The surgical stapling apparatus 1 (FIG. 1), with the anvil assembly 40 loaded with the anvil buttress 90, is ready for use. In aspects, as seen in FIG. 1, the staple cartridge assembly 60 is pre-loaded and/or loaded with a cartridge buttress 91.

In operation, with the loading unit 30 loaded with the anvil buttress 90, as described above, the surgical stapling apparatus 1 is used in accordance with methods known by those skilled in the art. Once the anvil and staple cartridge assemblies 40, 60 are clamped onto tissue, the surgical stapling apparatus 1 is fired, thereby stapling the anvil buttress 90 to the tissue. During firing, the knife blade 82 of the I-beam 84 travels distally through the tool assembly 34 and substantially simultaneously cuts and divides the tissue and the anvil buttress 90 disposed between the rows of formed staples 70. When firing is complete and the anvil and staple cartridge assemblies 40, 60 are unclamped, the anvil buttress 90, which is now stapled to the tissue, pulls away from the anvil assembly 40, and the tool assembly 34 can be removed from the surgical site. The used staple cartridge 64 may then be removed from the tool assembly 34 and replaced with a new staple cartridge 64. A new anvil buttress 90 may be installed onto the anvil assembly 40, as needed or desired, as described above.

Figure 11:
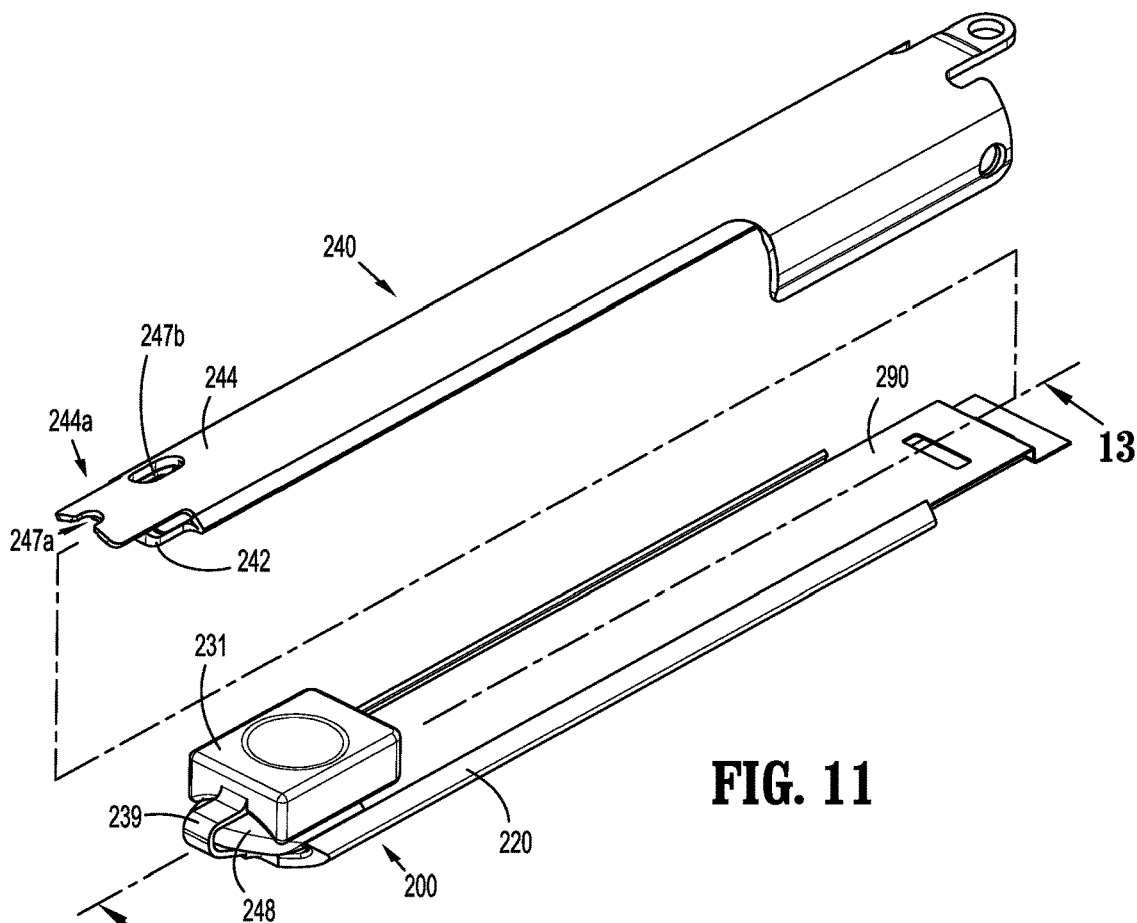
FIG. 11 is a perspective view, with parts separated, of an anvil assembly and an anvil loading tool loaded with an anvil tip and an anvil buttress in accordance with an aspect of the present disclosure.

Turning now to FIG. 11, an anvil assembly 240 and an anvil buttress loading tool 200 loaded with an anvil buttress 290 and an anvil tip 248 are shown in accordance with other aspects of the present disclosure is shown. The anvil tip 248 is releasably couplable to the anvil assembly 240 and is loaded onto the anvil assembly 240 with the anvil buttress 290 coupled thereto by the loading tool 200.

As shown in FIG. 11, in conjunction with FIGS. 14 and 15, the anvil assembly 240 includes an anvil plate 242 and a cover plate 244 secured over the anvil plate 242. An anvil tip 248 is separable from the anvil plate 242. The anvil plate 242 has a central longitudinal slot 241 formed therein and a plurality of staple forming pockets or cavities 243 defined in an inward or tissue facing surface thereof 246. A proximal end portion 242a of the anvil plate 242, which extends proximally of the staple forming pockets 243, includes a hook assembly 250 configured to secure a proximal end portion of a surgical buttress thereto.

The hook assembly 250 includes a pair of hooks 252, with each hook 252 disposed on opposed sides of the central longitudinal slot 241. Each hook 252 includes an arm 254 having a first or distal end portion 254a anchored or secured to the tissue facing surface 246 of the anvil plate 242 and a second or proximal end portion 254b including a finger 256 extending therefrom. The arm 254 extends upwardly away from the tissue facing surface 246 such that the finger 256 extends proximally and in spaced relation relative to the tissue facing surface 246 of the anvil assembly 240.

The cover plate 244 includes a notch 247a defined in a distal end 244a thereof and an opening 247b defined therethrough that is in registration with a groove 242c (FIG. 22) defined through the anvil plate 242.

The anvil tip 248 has a curved leading end 248a and a pair of legs 248c extending proximally from the curved leading end 248a. The pair of legs 248c are configured to receive the anvil plate 242 therebetween. A pocket 260 is defined in the anvil tip 248. The pocket 260 includes a curved surface 262 and longitudinal side slots 263 defined in opposed sides of pocket 260. An opening 265 extends through the curved surface 262, and includes a spherical distal region 265a and a slotted proximal region 265b.

A cantilever beam 266 extends proximally from the curved surface 262 between the pair of legs 248c. The cantilever beam 266 includes a catch 268 disposed at a proximal end 266a thereof. The catch 268 includes an engagement surface 268a to connect the anvil tip 248 to the anvil plate 242, and a cam surface 268b for deflecting the cantilever beam 266 laterally to disconnect the anvil tip 248 from the anvil plate 242.

Figure 12:
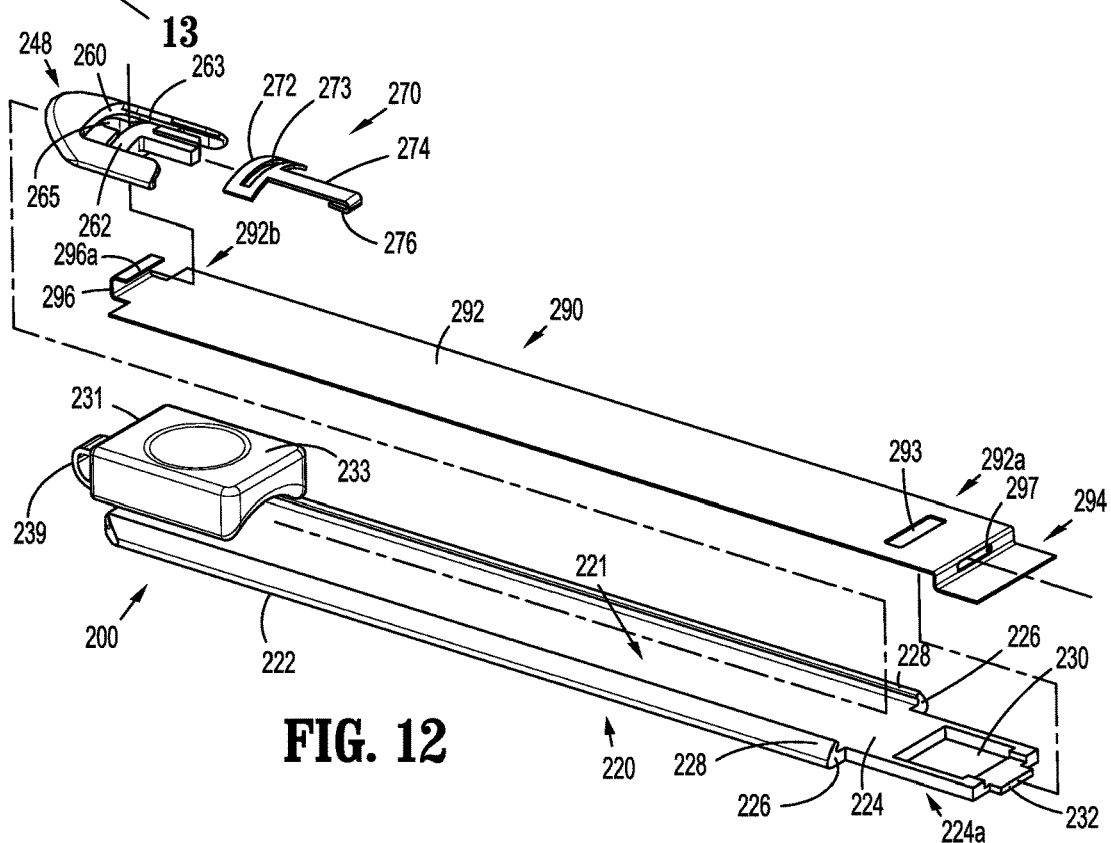
FIG. 12 is a perspective view, with parts separated, of the anvil loading tool, the anvil tip, and the anvil buttress of FIG. 11.
Figure 16:
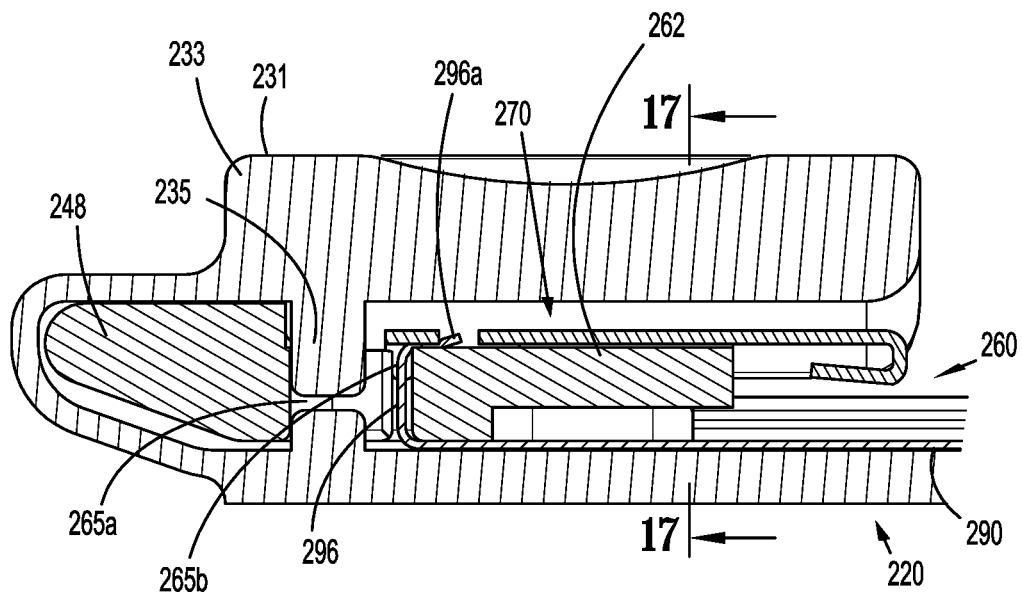
FIG. 16 is a close-up view of a distal end portion of the anvil buttress loading tool of FIG. 11.
Figure 23:
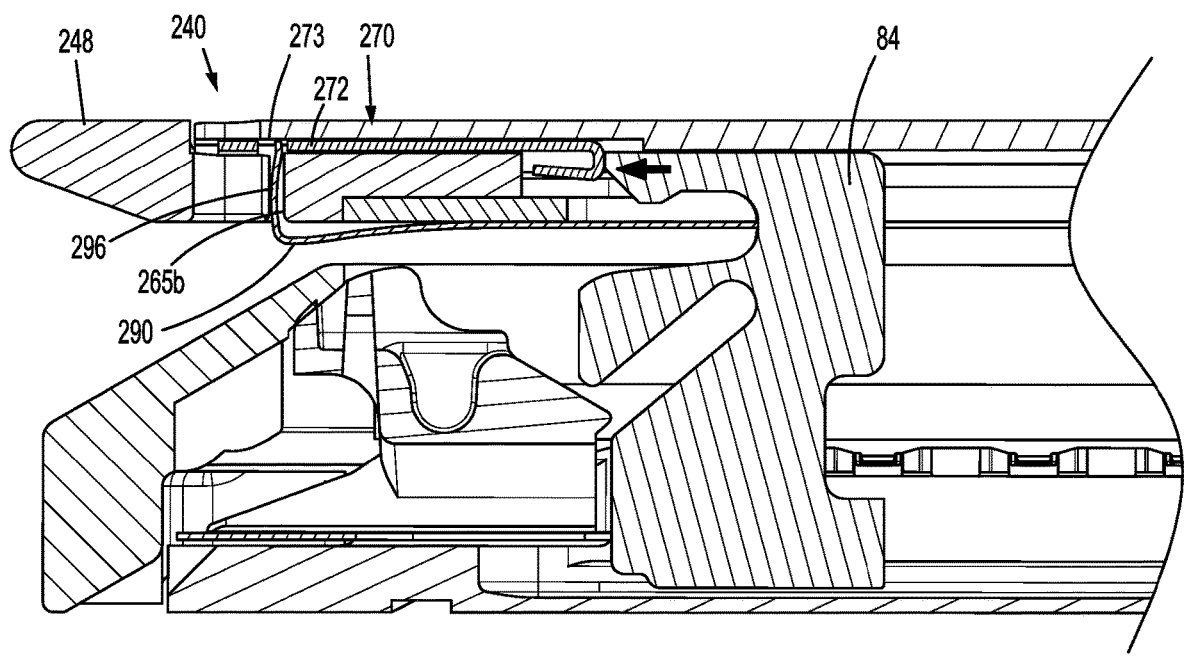
FIG. 23 is a cross-sectional view of the surgical stapling apparatus of FIG. 1, including the anvil assembly and the anvil buttress of FIG. 21, during a firing stroke of the surgical stapling apparatus.

Referring now to FIG. 12, the anvil tip 248 includes a retention assembly 270 configured to secure a distal end portion 292b of the anvil buttress 290 thereto. The retention assembly 270 includes a plate 272 and an elongated bar 274 extending proximally from the plate 272. The elongated bar 274 terminates in a curved tail 276. The plate 272 is contoured (e.g., curved) for positioning within the pocket 260 defined in the anvil tip 248. The plate 272 is positionable against the curved surface 262 of the anvil tip 248 with longitudinal edges of the plate 272 received within the longitudinal side slots 263 of the pocket 260 and is slidable therein between proximal and distal positions. The plate 272 includes a slot 273 defined therethrough that is configured to align with the slotted proximal region 265b of the opening 265 extending through the curved surface 262 of the anvil tip 248 when the plate 272 is moved to the distal position. The elongated bar 274 is configured to be engaged by the I-beam 84 (FIG. 2) of the drive assembly 80 during a firing stroke to slide the retention assembly 270 from the proximal position (biased position, as seen in FIG. 16) to the distal position (as seen in FIG. 23). The curved tail 276 of the retention assembly 270 may be deformable to allow the retention assembly 270 to move between the proximal and distal positions.

As shown in FIGS. 11-13, the anvil buttress 290 includes a body 292 having a proximal end portion 292a including a proximal window 293 defined therethrough and a stepped proximal tab 294 extending therefrom. The stepped proximal tab 294 includes an opening 297 defined therethrough. The body 292 has a distal end portion 292b including a distal tab 296 extending therefrom. The distal tab 296 has a generally C-shaped configuration including a lip 296a extending substantially parallel to the body 292 in spaced relation relative thereto.

With continued reference to FIGS. 11-13, the anvil buttress loading tool 200 includes a carrier 220, a retainer 231, and a tether 239 interconnecting the carrier 220 and the retainer 231. The tether 239 is a flexible strap, cord, band, rope, cable, etc. about which the retainer 231 can move relative to the carrier 220. The retainer 231 has a base 233 and a peg 235 (FIG. 16) extending from the base 233. The carrier 220 includes a housing 222 having a support surface 224 and longitudinal rails 226 extending from opposed sides of the support surface 224, with each of the longitudinal rails 226 includes a flange 228. A cavity 221 is defined in the carrier 220 by the support surface 224 and the longitudinal rails 226. The support surface 224 includes a proximal end portion 224a extending proximally beyond the longitudinal rails 226. The proximal end portion 224a includes a window 230 defined therethrough and a proximal protrusion 232 extending proximally therefrom.

Figure 17:
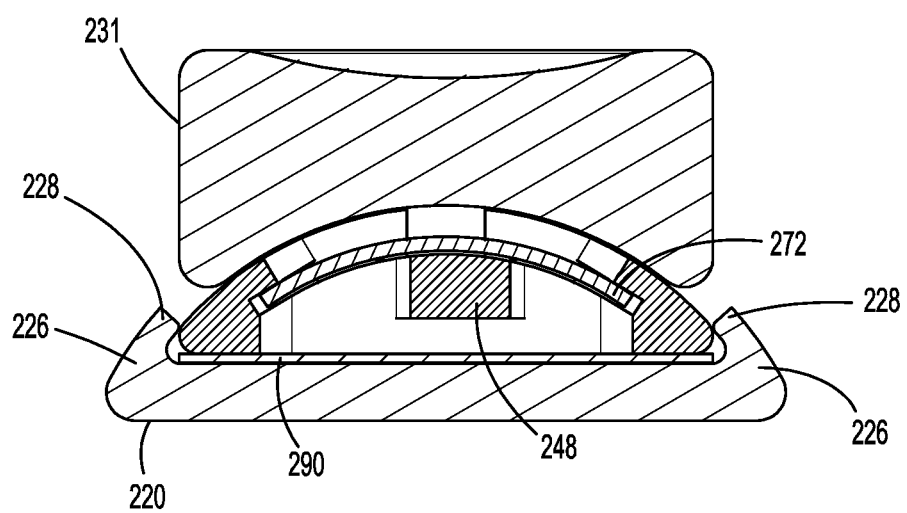
FIG. 17 is a cross-sectional view of the anvil buttress loading tool of FIG. 16, taken along section line 17-17 of FIG. 16.

In a method of loading the loading tool 200 with the anvil buttress 290 and the anvil tip 248, the body 292 of the anvil buttress 290 is placed against the support surface 224 of the carrier 220 such that opening 297 defined through the proximal tab 294 engages the proximal protrusion 232 of the support surface 224. The anvil tip 248 is placed into a distal end portion 220b of the carrier 220 by sliding the anvil tip 248 through the cavity 221 of the carrier 220 such that longitudinal edges of the anvil tip 248 engage the flanges 228 of the longitudinal rails 226, as seen in FIG. 17. During positioning of the anvil tip 248 within the carrier 220, the distal tab 296 of the anvil buttress 290 is threaded through the slotted proximal region 265b of the opening 265 defined in the anvil plate 248 such that a terminal end 296a of the distal tab 296 rests against the curved surface 262. The retention assembly 270 is then placed into the pocket 260 of the anvil tip 248, with the plate 272 positioned over the curved surface 262, capturing the distal tab 296 of the anvil buttress 290 therebetween, as shown in FIG. 16. The retainer 231 of the loading tool 200 is then placed over the anvil tip 248 such that the peg 235 of the retainer 231 engages the spherical distal region 265a of the opening 265 defined through the anvil tip 248 to retain the anvil buttress 290 and the anvil tip 248 on the loading tool 200. In the loaded configuration, the proximal end portion 292a of the anvil buttress 290 is engaged with the proximal protrusion 232 extending from the support surface 224 of the carrier 220, and the distal end portion 292b of the anvil buttress 290 is captured within the anvil tip 248 by the retention assembly 270.

Figure 18:
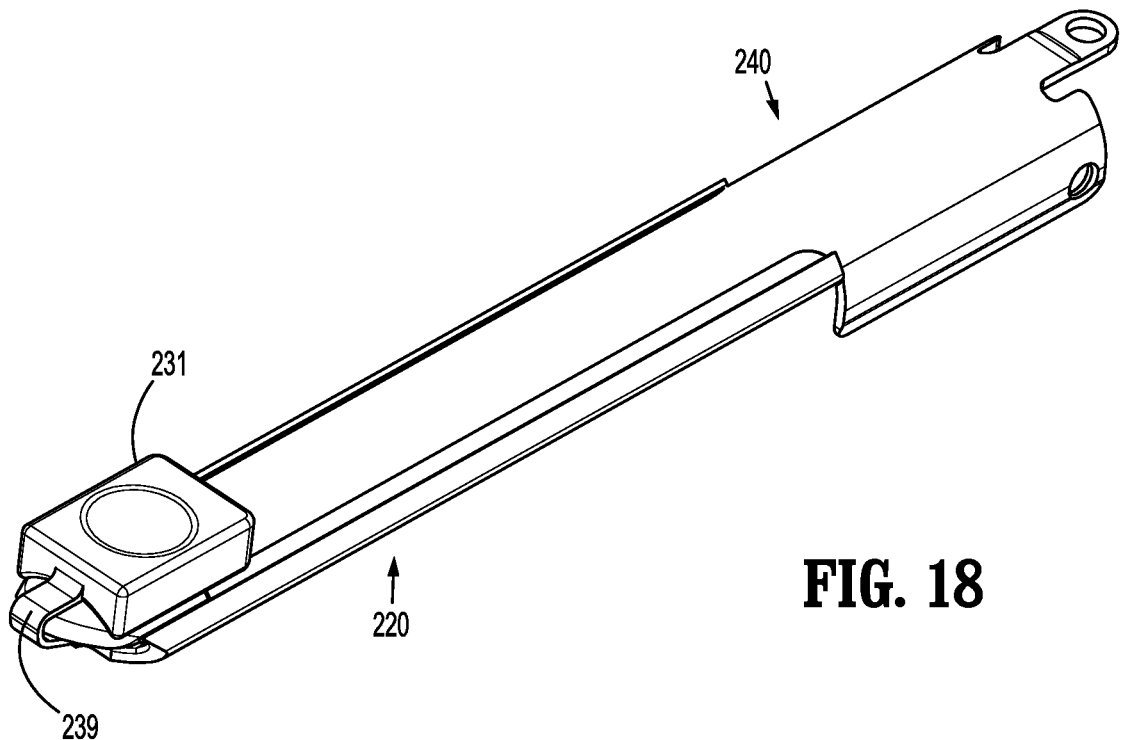
FIG. 18 is a top, perspective view of the anvil assembly of FIG. 11 advanced into the anvil buttress loading tool of FIG. 11.
Figure 19:
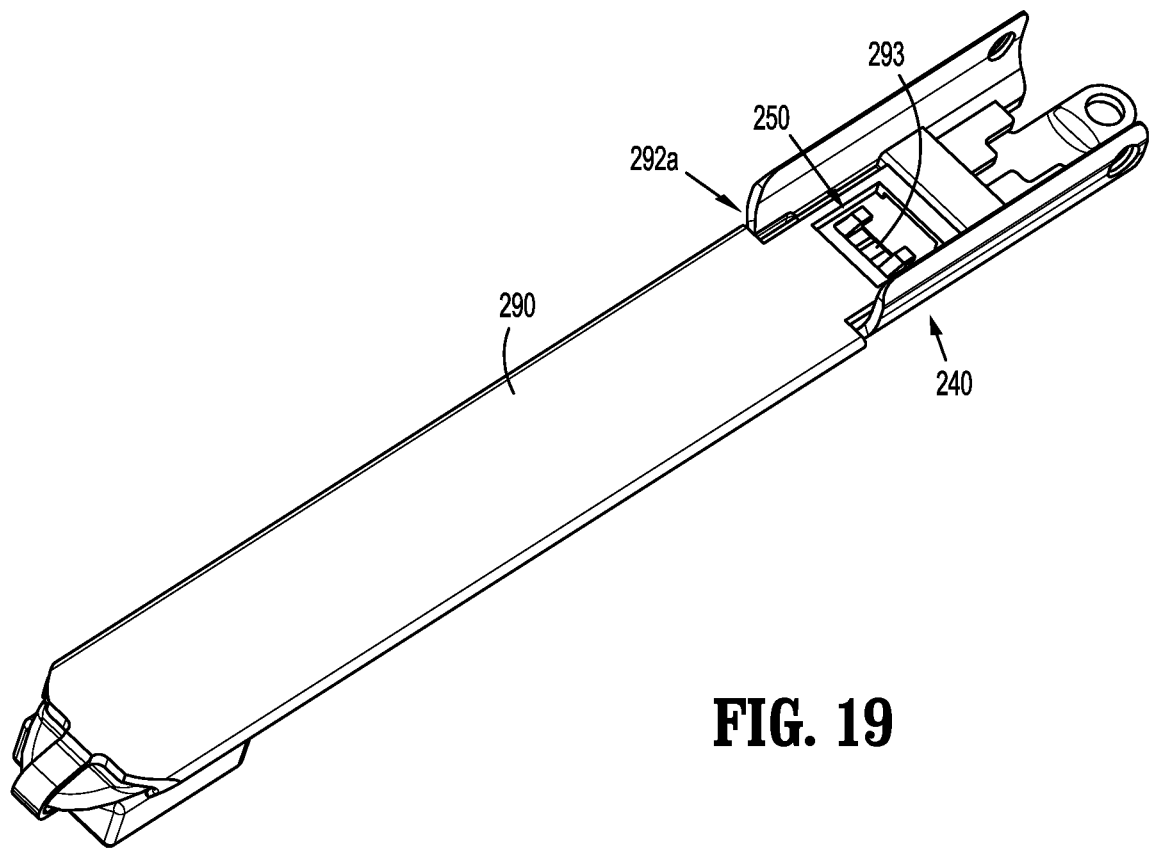
FIG. 19 is a bottom perspective view of the anvil assembly and the anvil buttress loading tool of FIG. 18.
Figure 22:
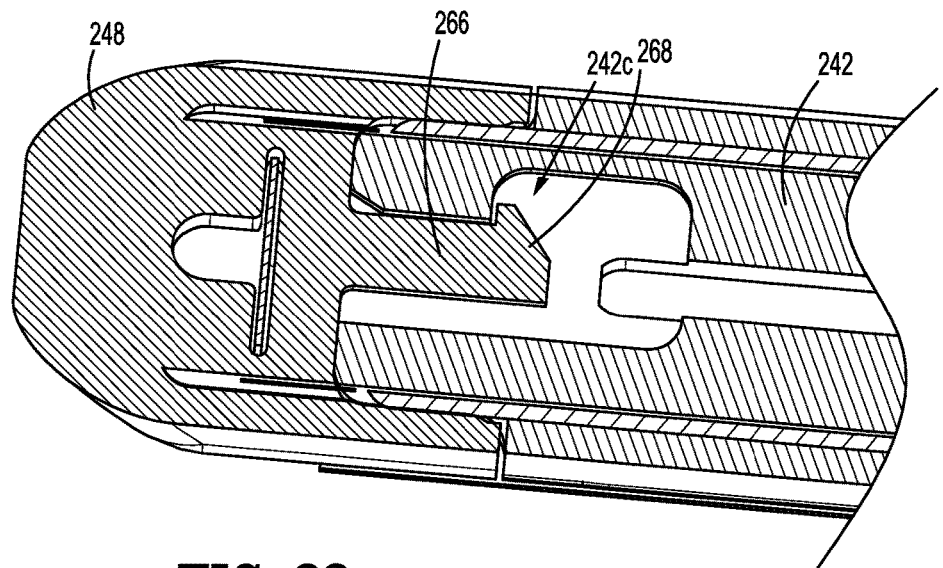
FIG. 22 is a cross-sectional view of a distal end portion of the anvil assembly of FIG. 21, taken along section line 22-22 of FIG. 21.

In a method of loading the anvil assembly 240 with the anvil buttress 290 and the anvil tip 248, the anvil plate 242 and the anvil cover 244 are slid distally into the cavity 221 of the carrier 220 such that the tissue facing surface 246 of the anvil plate 242 is adjacent to or in contact with the anvil buttress 290. The anvil assembly 240 is guided through and retained within the cavity 221 of the carrier 220 by the support surface 224, the longitudinal rails 226, and the flanges 228. The anvil assembly 240 is slid distally until it is fully advanced with the carrier 220, as shown in FIGS. 18 and 19, and the catch 268 of the beam 266 engages a groove 242c defined in the anvil plate 242, as seen in FIG. 22, locking the anvil tip 248 to the anvil plate 242. As seen in FIG. 19, the proximal window 293 of the anvil buttress 290 is aligned with the hook assembly 250 of the anvil plate 242 when fully inserted into the loading tool 200 such that the hooks 252 extend through the proximal window 293 and retain the proximal end portion 292a of the anvil buttress 290 to the anvil assembly 240.

The loading tool 200 is separated from the anvil assembly 240 by removing (e.g., flipping) the retainer 231 out of the anvil tip 248, as shown in FIG. 20, and sliding the loading tool 200 and/or the anvil assembly 240 away from each other. As shown in FIG. 21, the proximal end portion 292a of the anvil buttress 290 is retained on the anvil assembly 240 by engagement of the hook assembly 250 through the proximal window 293 and the distal end portion 292b of the anvil buttress 290 is retained on the anvil assembly 240 by the anvil tip 248. Specifically, the distal end portion 292b of the anvil buttress 290 is retained on the anvil assembly 240 by engagement of the retention assembly 270 with the distal tab 296 as described above.

Figure 24:
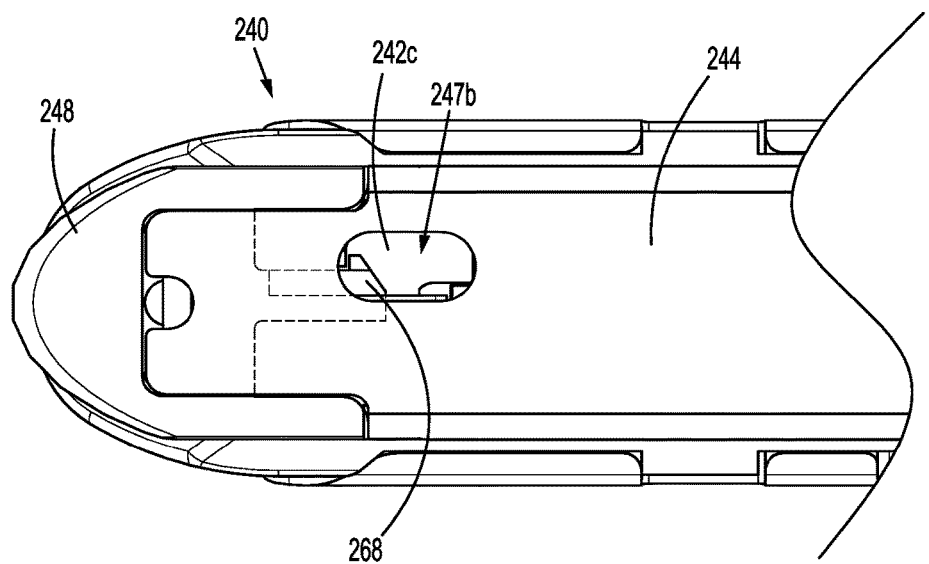
FIG. 24 is a top view of a distal end portion of the anvil assembly of FIG. 21.

The surgical stapling apparatus 1 (FIG. 1), with the anvil assembly 240 loaded with the anvil buttress 290, is ready for use. In use, as shown in FIG. 23, at the end of a firing stroke, the I-beam 84 cams the retention assembly 270 distally, aligning the slot 273 of the plate 272 with the slotted proximal region 265b of the anvil tip 248 and releasing the distal tab 296 of the anvil buttress 290. After use, the peg 244 (FIG. 20) on the loading tool 200 may be utilized through the opening 247b defined through the cover plate 244, as seen in FIG. 24, to move the catch 268 out of the groove 242c of the anvil plate 242 to release the anvil tip 248 from the anvil assembly 240.

Figure 25:
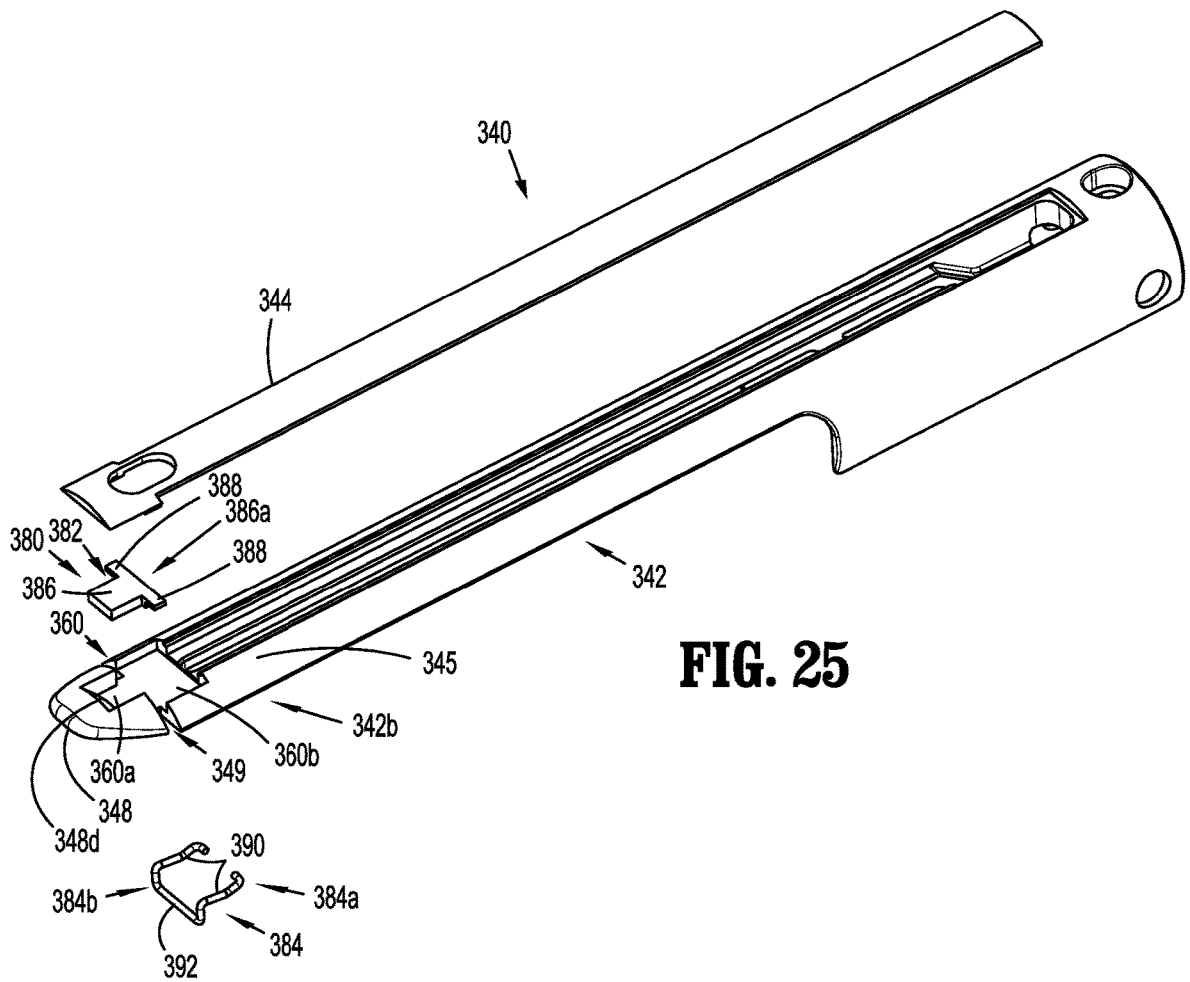
FIG. 25 is a perspective view, with parts separated, of an anvil assembly in accordance with another aspect of the present disclosure.

Turning now to FIGS. 25 and 26, an anvil assembly 340 in accordance with yet another aspect of the present disclosure is shown. The anvil assembly 340 includes an anvil plate 342 and a cover plate 344 secured over the anvil plate 342. The anvil plate 342 has a central longitudinal slot 341 formed therein and a plurality of staple forming pockets or cavities 343 defined in an inward or tissue facing surface thereof 346, with an anvil tip 348 extending distal to the staple forming pockets 343. A pair of recesses 349 are defined in side edges of the anvil assembly 340 between the anvil plate 342 and the anvil tip 348. A proximal portion 342a of the anvil plate 342, which extends proximally of the staple forming pockets 343, includes a hook assembly 350 configured to secure a proximal end portion of a surgical buttress thereto. The anvil tip 348 includes a spring assembly 380 configured to secure a distal end portion of the surgical buttress thereto.

The hook assembly 350 includes a pair of hooks 352, with each hook 352 disposed on opposed sides of the central longitudinal slot 341. Each hook 352 includes an arm 354 having a first or distal end portion 354a anchored or secured to the tissue facing surface 346 of the anvil plate 342 and a second or proximal end portion 354b including a finger 356 extending therefrom. The arm 354 extends upwardly away from the tissue facing surface 346 such that the finger 356 extends proximally and in spaced relation relative to the tissue facing surface 346 of the anvil assembly 340.

A cavity 360 is defined within the anvil tip 348 and the distal end portion 342b of the anvil plate 342. The cavity 360 is open to an outer surface 345 of the anvil assembly 340 at the anvil tip 348 and covered by the cover plate 344 at the distal end portion 342b of the anvil plate 342. A dimension or width of a distal portion 360a of the cavity 360 defined in the anvil tip 348 is smaller than a dimension or width of a proximal portion 360b of the cavity 360 defined in the anvil plate 342. The anvil tip 348 includes a sloped surface 348d extending from the outer surface 345 into the cavity 360.

The spring assembly 380 includes a slider 382 and a spring 384. The slider 382 includes a body 386 and a pair of wings 388 extending laterally from a proximal portion 386a of the body 386. The spring 384 has a rigid structure (e.g., a wire frame) having a proximal end portion 384a including a pair of legs 390 configured to extend around the proximal portion 386a of the body 386 of the slider 382 and a distal end portion 384b including a bridge 392 interconnecting the pair of legs 390.

Figure 28:
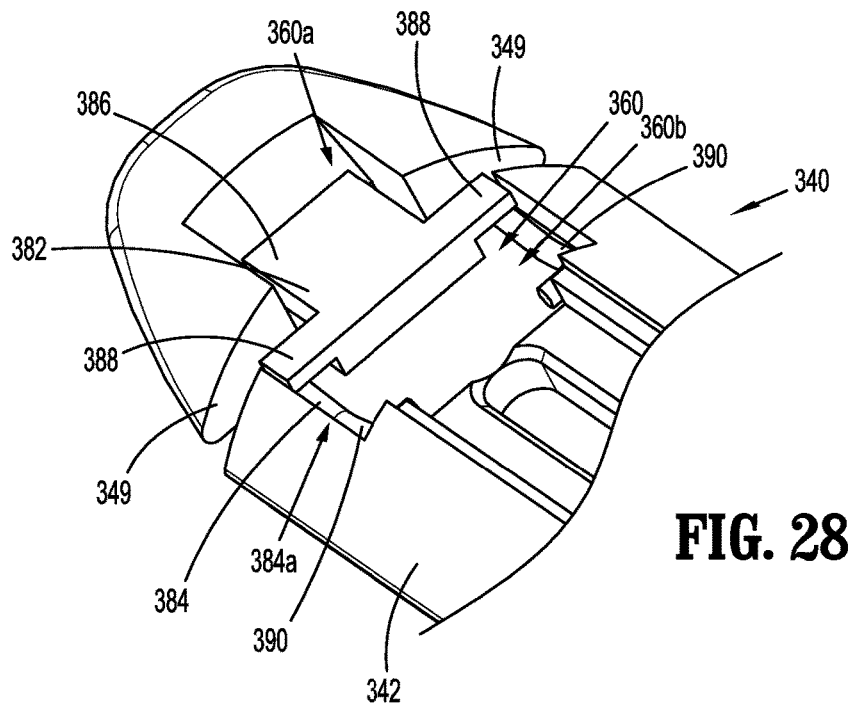
FIG. 28 is a top, perspective view of the anvil assembly of FIG. 25, with the cover plate removed, illustrating a spring assembly disposed within the anvil assembly.
Figure 29:
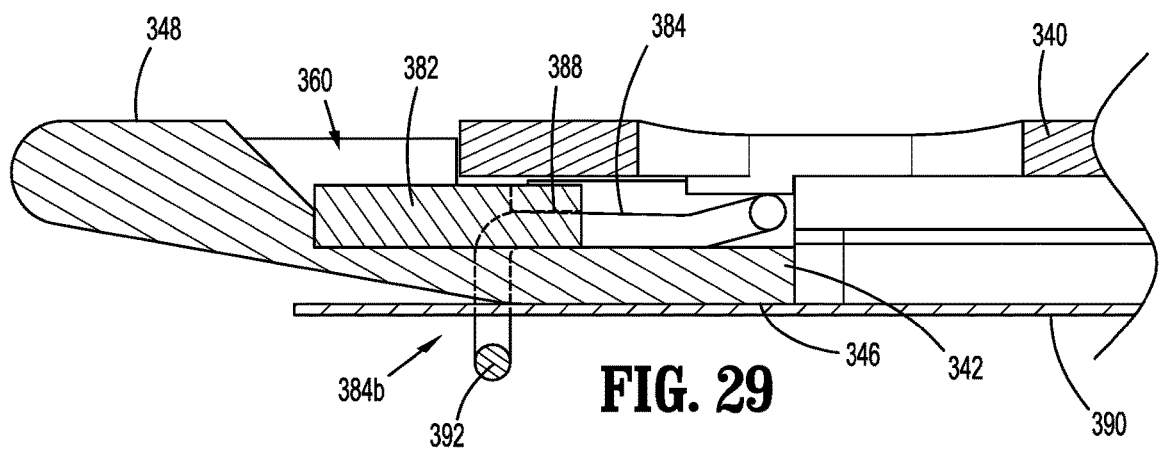
FIG. 29 is a cross-sectional view of the anvil assembly of FIG. 28, shown with the spring assembly disposed in an unclamped position.

As shown in FIG. 28, the spring 384 is positioned in the cavity 360 of the anvil assembly 340 with the proximal end portion 384a disposed within proximal portion 360b of the cavity 360. Portions of the pair of legs 390 extend through the pair of recesses 349 defined in the anvil plate 342 such that the distal end portion 384b of the spring 384 is disposed outside of the cavity 360 and across the tissue facing surface 346 of the anvil plate 342 (FIG. 29). The slider 382 is positioned within the cavity 360 with the pair of wings 388 positioned over the pair of legs 390 of the spring 384 within the proximal portion 360b of the cavity 360 and the body 386 extending distally into the distal portion 360a of the cavity 360.

Figure 30:
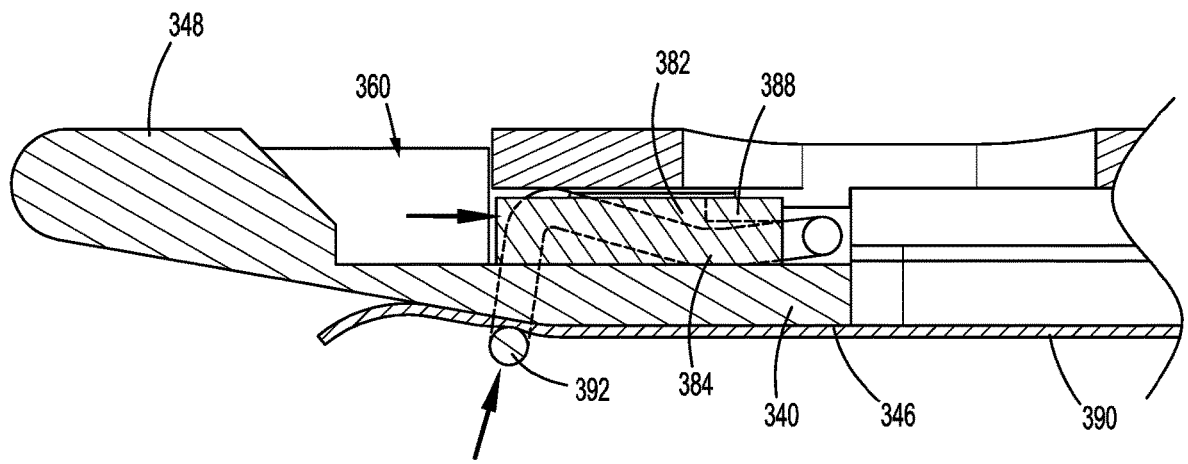
FIG. 30 is a cross-sectional view of the anvil assembly of FIG. 28, shown with the spring assembly disposed in a clamped position.

The spring assembly 380 has an unclamped or unload position, as shown in FIG. 29, in which the slider 382 is disposed in a distal position and the pair of wings 388 of the slider 382 cams the spring 384 distally such that the bridge 392 extends away from and in spaced relation relative to the tissue facing surface 346 of the anvil assembly 340. The spring assembly 380 also has an clamped or loaded position, as shown in FIG. 30, in which the slider 382 is disposed in a proximal position and the pair of wings 388 cams the spring 384 upwardly within the cavity 360 to move the bridge 392 into contact with the tissue facing surface 346 of the anvil assembly 340.

As shown in FIG. 27, the anvil buttress 390 includes a body 392 having a proximal end portion 392a including a proximal window 393 defined therethrough and a distal end portion 392b including a distal tab 396 extending therefrom. The distal tab 396 has a smaller dimension or width than the body 392.

Figure 31:
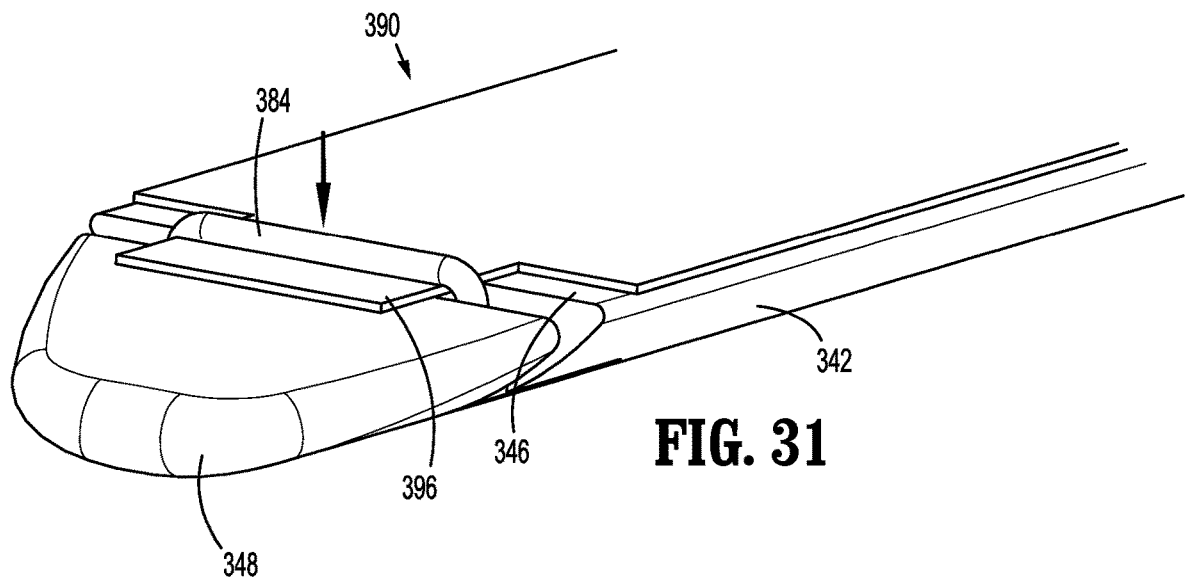
FIG. 31 is a perspective view of a distal end portion of the anvil assembly of FIG. 30.

In a method of loading the anvil assembly 340 with the anvil buttress 390, the spring assembly 380 is positioned in the unload position as shown in FIGS. 26, 27, and 29. The body 392 of the anvil buttress 390 is placed against the tissue facing surface 346 of the anvil assembly 340 such that the proximal window 393 engages the hook assembly 350 and the distal tab 396 is positioned between the tissue facing surface 246 and the bridge 392 of the spring 384. The slider 382 is then moved to the load position, as seen in FIGS. 30 and 31, by accessing the slider 382 through the open distal portion 360a of the cavity 360 and pushing the slider 382 proximally, for example, with a loading tool (not shown).

Figure 32:
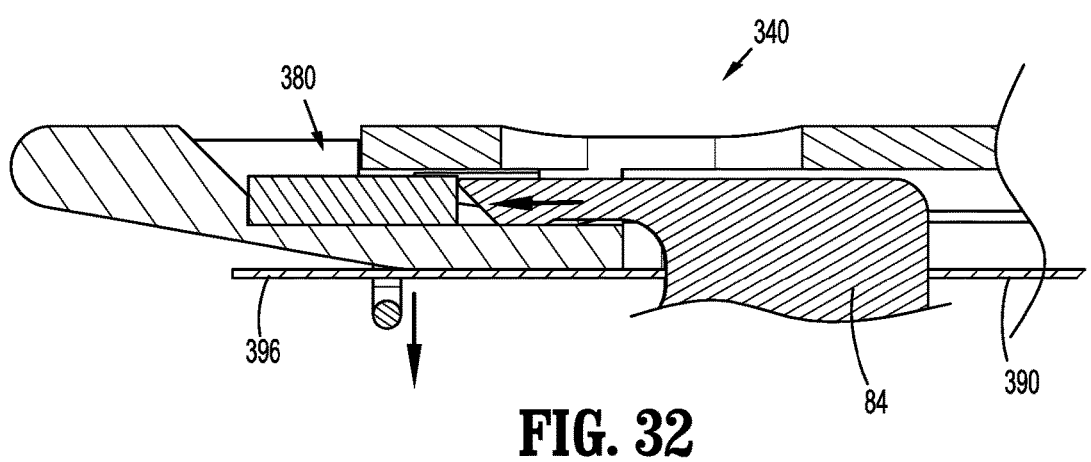
FIG. 32 is a cross-sectional view of the distal end portion of the anvil assembly of FIG. 29, during a firing stroke of the surgical stapling apparatus of FIG. 1.

The surgical stapling apparatus 1 (FIG. 1), with the anvil assembly 340 loaded with the anvil buttress 390, is ready for use. In use, as shown in FIG. 32, at the end of a firing stroke, the I-beam 84 cams the spring assembly 380 distally to the unload position, freeing the distal tab 396 of the anvil buttress 390 from the anvil assembly 340. The spring assembly 380 remains in the unload position until a new anvil buttress 390 is loaded onto the anvil assembly 340, as described above.

Figure 33:
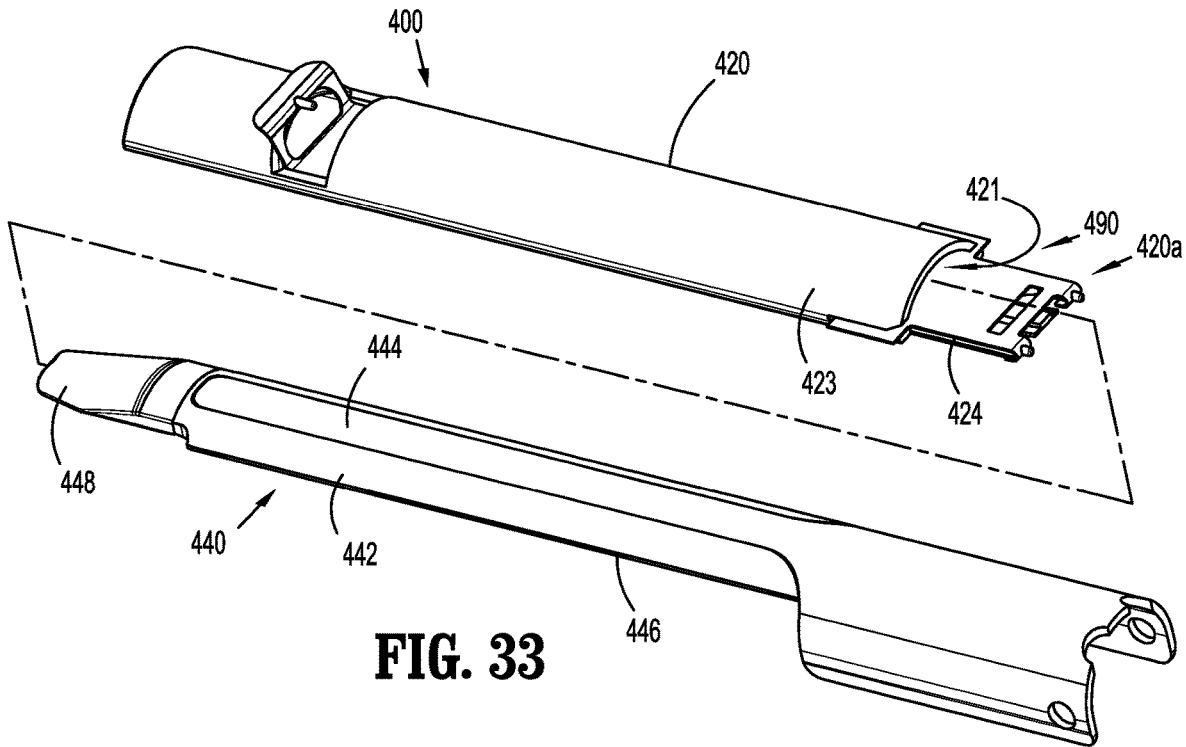
FIG. 33 is a perspective view, with parts separated, of an anvil assembly and an anvil loading tool loaded with an anvil buttress in accordance with yet another aspect of the present disclosure.
Figure 34:
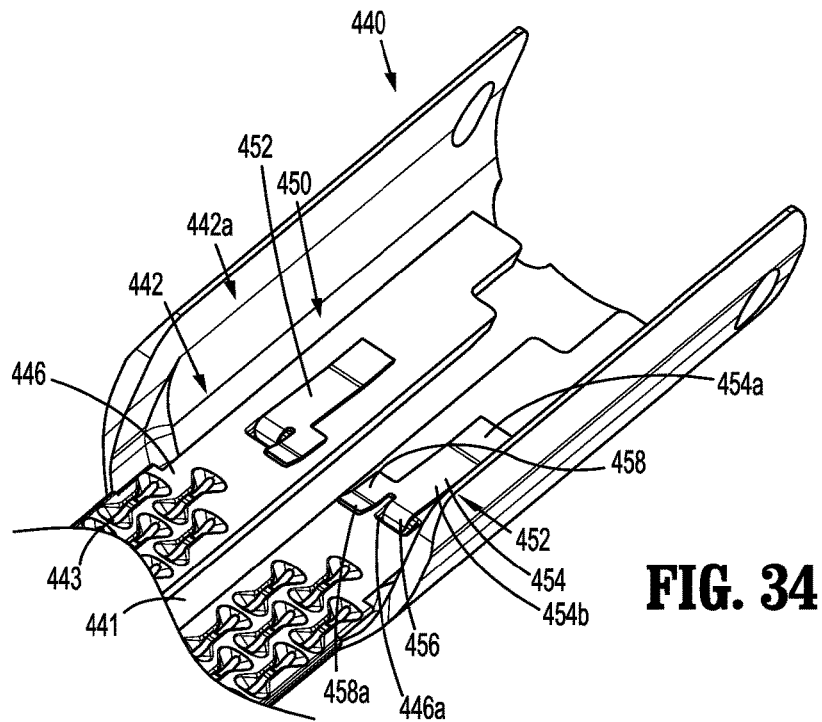
FIG. 34 is a bottom, perspective view of a proximal end portion of the anvil assembly of FIG. 33.

Referring now to FIG. 33, an anvil assembly 440 and an anvil buttress loading tool 400, in accordance with another aspect of the present disclosure, is shown. The anvil assembly 440 includes an anvil plate 442 and a cover plate 444 secured over the anvil plate 442. As shown in FIG. 34, in conjunction with FIG. 33, the anvil plate 442 has a central longitudinal slot 441 formed therein and a plurality of staple forming pockets or cavities 443 defined in an inward or tissue facing surface thereof 446, with an anvil tip 448 extending distal to the staple forming pockets 443. A proximal portion 442a of the anvil plate 442, which extends proximally of the staple forming pockets 443, includes a spring and hook assembly 450 configured to secure a proximal end portion of a surgical buttress thereto.

The spring and hook assembly 450 includes a pair of spring and hook members 452, with each spring and hook members 452 disposed on opposed sides of the central longitudinal slot 441. Each spring and hook member 452 includes an arm 454 having a first or proximal end portion 454a anchored or secured to the tissue facing surface 446 of the anvil plate 442 and a second or distal end portion 454b including first and second fingers 456, 458 extending therefrom. The first finger 456 is bent or curved relative to the arm 454 downwardly towards the tissue facing surface 446 such that a terminal end 456a (FIG. 39) of the first finger 456 is biased into a notch 446a defined in the tissue facing surface 446. The second finger 458 is disposed laterally inwardly of the first finger 456 and is bent or curved upwardly away from the tissue facing surface 446 such that a terminal end 458a of the second finger 458 is biased in spaced relation relative to the tissue facing surface 446. Each arm 454 is hingedly or springedly connected to the anvil plate 452 at the proximal end portion 454a thereof such that when a force acts upon the second fingers 458, the second finger 458 is lifted off of the tissue facing surface 446 and the first finger 456 is moved out of the notch 446a.

Figure 35:
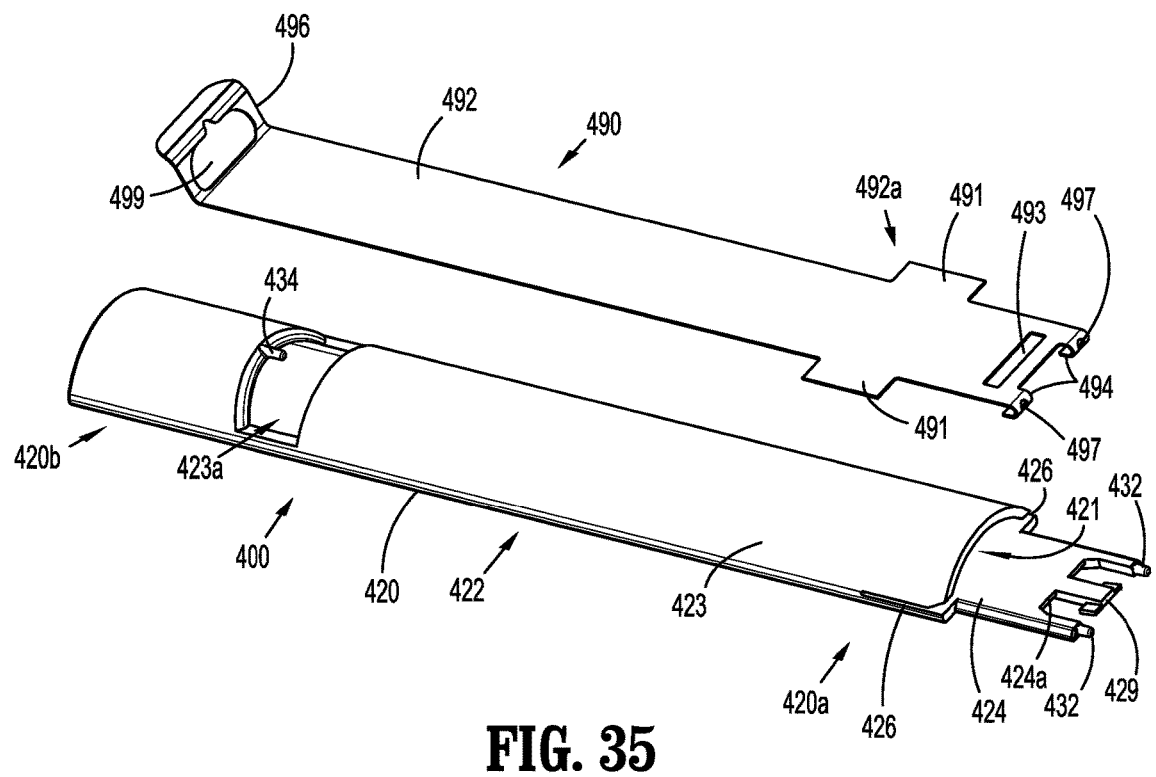
FIG. 35 is a perspective view, with parts separated, of the anvil buttress loading tool and the anvil buttress of FIG. 33.

As shown in FIG. 35, the anvil buttress 490 includes a body 492 having a pair of wings 491 extending laterally from a proximal end portion 492a thereof. A first or proximal window 493 is defined through the proximal end portion 492a of the body 492 proximal of the pair of wings 491. A pair of proximal tabs 494 extend proximally from the proximal end portion 492a of the body 492, with each proximal tab 494 defining an opening 497 therethrough. A distal tab 496 extends distally from the distal end portion 492b of the body 492 and defines an opening 499 therethrough.

Figure 36:
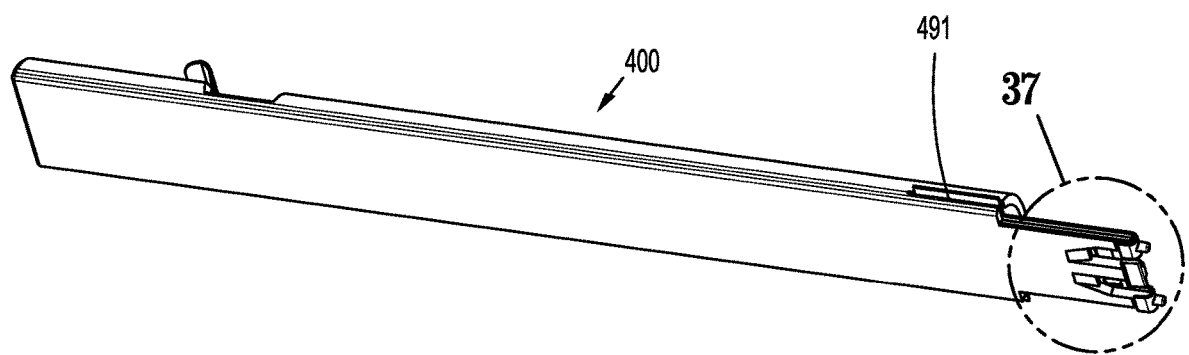
FIG. 36 is a bottom, perspective view of the anvil buttress loading tool and the anvil buttress of FIG. 33.

As shown in FIGS. 35-37, the anvil buttress loading tool 400 includes a carrier 420 is configured to releasably retain the anvil buttress 490 therein and to receive the anvil assembly 440 (FIG. 33) for loading of the anvil buttress 490 thereon. The carrier 420 includes a housing 422 having a support surface 424 and a cover 423 extending over the support surface 424. A cavity 421 is defined in the carrier 420 by the support surface 424 and the cover 423. A pair of slits 426 is defined between the support surface 424 and the cover 423 at a proximal end portion 420a of the carrier 420. The support surface 424 extends proximally beyond the cover 423 and includes a pair of proximal protrusions 432 extending proximally from a proximal end 424a of the support surface 424. A ramp 429 is disposed between the pair of proximal protrusions 342. The cover 423 includes an opening 423a defined therethrough at a distal end portion 420b of the carrier 420 and includes a distal protrusion 434 extending proximally into the opening 423a.

In a method of loading the loading tool 400 with the anvil buttress 490, the body 492 of the anvil buttress 490 is passed into the cavity 421 of the carrier 420 and positioned against the support surface 424 of the carrier 420 with the pair of wings 491 received within the pair of slits 426. With the body 492 of the anvil buttress 490 positioned on the support surface 424, the pair of proximal tabs 494 is aligned or in registration with the pair of proximal protrusions 432 of the support surface 424, and the distal tab 496 is aligned or in registration with the distal protrusion 434 of the cover 423. Accordingly, the proximal and distal end portions 492a, 492b of the anvil buttress 490 are manipulated to engage the pair of proximal tabs 494 with the pair of proximal protrusions 432 and the distal tab 496 through the opening 423a and into engagement with the distal protrusion 434.

Figure 41:
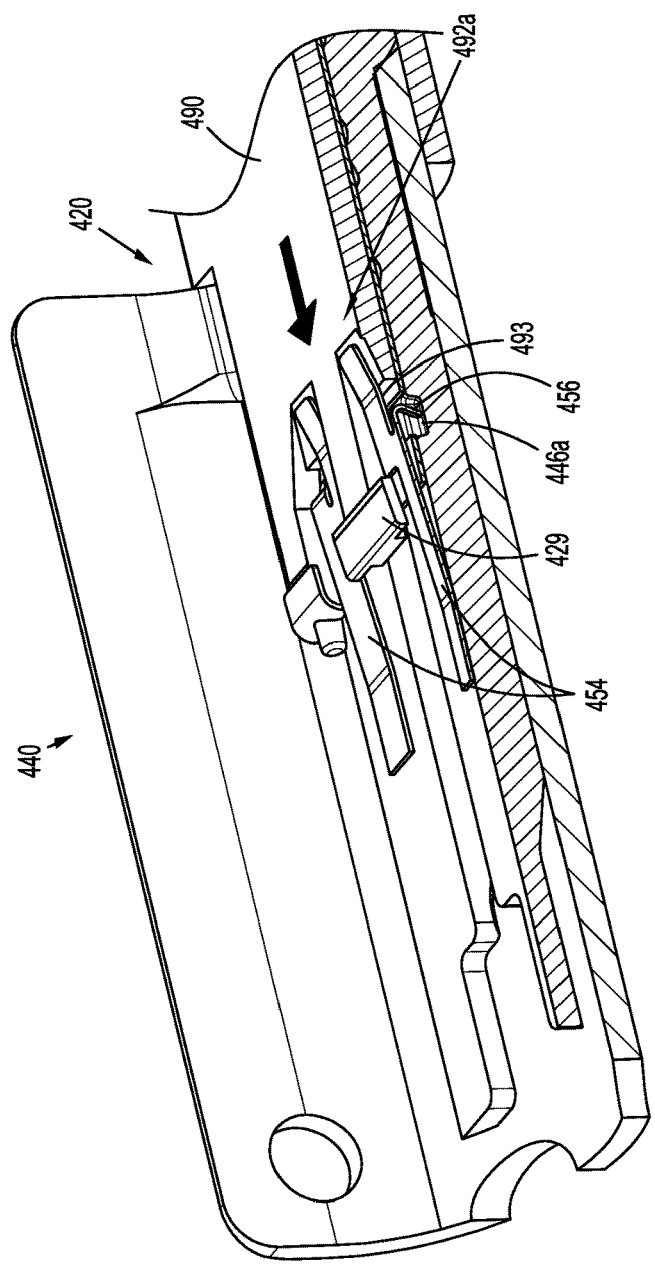

In a method of loading the anvil assembly 440 with the anvil buttress 490, as seen initially in FIG. 33, the anvil tip 448 of the anvil assembly 440 is aligned a proximal end 420a of the carrier 420 of the loading tool 400. The anvil assembly 440 is slid distally into the cavity 421 of the carrier 420 such that the tissue facing surface 446 of the anvil assembly 440 is adjacent to or in contact with the anvil buttress 490. The anvil assembly 440 is guided through and retained within the cavity 421 of the carrier 420 by the support surface 424 and the cover 423. The anvil assembly 440 is slid distally until the anvil tip 448 extends through the distal window 495 defined through the anvil buttress 490. During this sliding movement, the ramp 429 of the carrier 420 contacts the second fingers 548 of the spring and hook assembly 450, raising the second fingers 548 off of the tissue facing surface 446 of the anvil plate 442 and lifting the first fingers 456 out of the notches 446a defined in the tissue facing surface 446, as shown in FIGS. 39 and 40. Once the ramp 429 clears the second fingers 458, as shown in FIG. 41, the arms 454 snaps back down and the first fingers 456 extend through the proximal window 493 and re-enter the notches 446a thereby capturing the proximal end portion 492a of the anvil buttress 490 to the anvil assembly 440.

Figure 42:
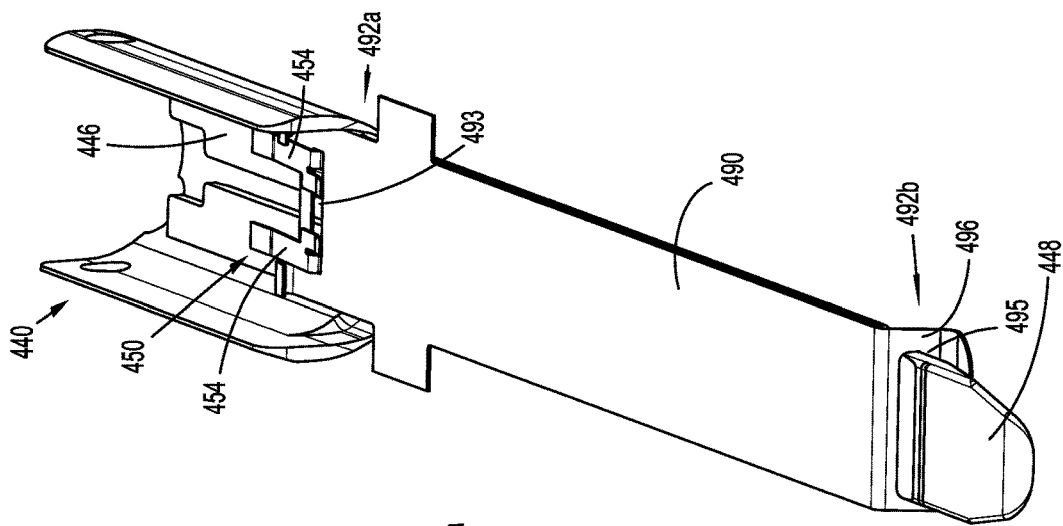
FIG. 42 is a bottom, perspective view of the anvil assembly of FIG. 33 loaded with the anvil buttress.

Once the anvil assembly 440 is fully advanced into the carrier 420 of the loading tool 400, as seen in FIG. 38, the loading tool 400 may be separated from the anvil assembly 440 by sliding the loading tool 400 and/or the anvil assembly 440 in opposite directions. As the anvil assembly 440 and the loading tool 400 are separated from each other, the arms 454 of the spring and hook assembly 450 elastically deform downwardly into the tissue facing surface 446 of the anvil assembly 440 until the ramp 429 passes thereover. The proximal end portion 492a of the anvil buttress 490 is retained on the anvil assembly 440 by engagement of the spring and hook assembly 450 through the proximal window 493 and the distal end portion 492b of the anvil buttress 490 is retained on the anvil assembly 440 by engagement of the distal tab 496 with the anvil tip 448 through the distal window 495, as seen in FIG. 42. The surgical stapling apparatus 1 (FIG. 1), with the anvil assembly 440 loaded with the anvil buttress 490, is ready for use.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be affected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. An anvil buttress loading system comprising:
an anvil assembly including an anvil plate and an anvil tip, the anvil plate having a tissue facing surface defining a central longitudinal slot and a plurality of staple forming pockets therein, a proximal end portion of the tissue facing surface including a hook assembly, the hook assembly including a pair of hooks disposed on opposed sides of the central longitudinal slot, each hook of the pair of hooks including an arm having a first end anchored to the tissue facing surface and a second end including a finger extending therefrom, a terminal end of the finger is biased against the tissue facing surface and movable relative to the tissue facing surface;
an anvil buttress loading tool including a carrier defining a cavity therein, the carrier having a support surface, a proximal end portion of the carrier including a pair of proximal protrusions and a distal end portion of the carrier including a distal protrusion; and
an anvil buttress including a body, a pair of proximal tabs extending proximally from the body, and a distal tab extending distally from the body,
wherein:
the body of the anvil buttress is positionable on the support surface of the anvil buttress loading tool with the pair of proximal tabs engaged with the pair of proximal protrusions and the distal tab engaged with the distal protrusion to retain the anvil buttress on the anvil buttress loading unit;
the body of the anvil buttress is positionable on the tissue facing surface of the anvil assembly with a proximal end portion of the body engaged with the hook assembly and a distal end portion engaged with the anvil tip to retain the anvil buttress on the anvil assembly; and
the anvil buttress is transferrable from the anvil buttress loading tool to the anvil assembly.

2. The anvil buttress loading system according to claim 1, wherein the first end of the arm is anchored to the tissue facing surface at a proximal end thereof and the second end is disposed distal thereto.

3. The anvil buttress loading system according to claim 1, wherein the anvil buttress has a proximal window defined in the proximal end portion of the body, the proximal window configured to receive the fingers of the pair of hooks therethrough.

4. The anvil buttress loading system according to claim 1, wherein the anvil buttress includes a distal window defined through a distal end portion of the anvil buttress, the distal window configured to receive the anvil tip therethrough.

5. The anvil buttress loading system according to claim 1, wherein the carrier of the anvil buttress loading tool includes longitudinal rails extending from opposed sides of the support surface, the anvil assembly positionable between the longitudinal rails with the tissue facing surface adjacent to the support surface.

6. The anvil buttress loading system according to claim 5, wherein the carrier of the anvil buttress loading tool includes a transverse rail extending across distal ends of the longitudinal rails and over the support surface defining a distal opening into the cavity.

7. The anvil buttress loading system according to claim 1, wherein the finger of each of the pair of hooks is curved relative to the arm.

8. The anvil buttress loading system according to claim 1, wherein the anvil buttress loading tool includes a handle secured to the carrier.

9. The anvil buttress loading system according to claim 1, wherein each proximal tab of the pair of proximal tabs of the anvil buttress defines an opening therethrough, and the distal tab of the anvil buttress defines an opening therethrough.

10. An anvil buttress loading assembly comprising:
   an anvil buttress loading tool including a carrier defining a cavity therein, the carrier having a support surface, longitudinal rails extending from opposed sides of the support surface, and a transverse rail extending across distal ends of the longitudinal rails and over the support surface defining a distal opening into the cavity, a proximal end portion of the carrier including a pair of proximal protrusions and a distal end portion of the carrier including a distal protrusion; and
   an anvil buttress including a body, a pair of proximal tabs extending proximally from the body, and a distal tab extending distally from the body,
   wherein the body of the anvil buttress is positioned on the support surface, the pair of proximal tabs engaged with the pair of proximal protrusions, and wherein the distal tab is engaged with the distal protrusion.

11. The anvil buttress loading assembly according to claim 10, wherein a plurality of axially spaced and opposed tabs extend from the longitudinal rails and over the support surface.

12. The anvil buttress loading assembly according to claim 10, wherein the distal protrusion extends from the transverse rail.

13. The anvil buttress loading assembly according to claim 10, wherein the anvil buttress includes a distal window defined through a distal end portion of the body, the distal window aligned with the distal opening of the carrier.

14. The anvil buttress loading assembly according to claim 10, wherein the anvil buttress loading tool includes a handle secured to the carrier.

15. The anvil buttress loading assembly according to claim 10, wherein each proximal tab of the pair of proximal tabs of the anvil buttress defines an opening therethrough, and the distal tab of the anvil buttress defines an opening therethrough.

16. A loading unit comprising:
   a staple cartridge assembly;
   an anvil assembly including an anvil plate and an anvil tip, the anvil plate having a tissue facing surface defining a central longitudinal slot and a plurality of staple forming pockets therein, a proximal end portion of the tissue facing surface including a hook assembly, the hook assembly including a pair of hooks disposed on opposed sides of the central longitudinal slot, each hook of the pair of hooks including an arm having a first end anchored to the tissue facing surface and a second end including a finger extending therefrom, a terminal end of the finger is biased against the tissue facing surface and movable relative to the tissue facing surface; and
   an anvil buttress including a body having a proximal end portion releasably coupled to the anvil assembly by the hook assembly.

17. The loading unit according to claim 16, wherein the first end of the arm is anchored to the tissue facing surface at a proximal end thereof and the second end is disposed distal thereto.

18. The loading unit according to claim 16, wherein the anvil buttress has a proximal window defined in the proximal end portion of the body, the fingers of the pair of hooks extending through the proximal window and positioned against the tissue facing surface.

19. The loading unit according to claim 16, wherein the anvil buttress includes a distal window defined through a distal end portion of the body, the distal end portion of the anvil buttress coupled to the anvil assembly by engagement of the distal window around the anvil tip.

20. The loading unit according to claim 16, wherein the finger of each of the pair of hooks is curved relative to the arm.

* * * * *